US008778084B2

(12) United States Patent
Nguyen et al.

(10) Patent No.: US 8,778,084 B2
(45) Date of Patent: Jul. 15, 2014

(54) METHOD AND APPARATUS FOR TREATING A CELLULOSIC FEEDSTOCK

(75) Inventors: Quang A. Nguyen, Chesterfield, MO (US); Sunalie N. Hillier, Georgetown (CA); Murray J. Burke, Oakville (CA)

(73) Assignee: Abengoa Bioenergy New Technologies, LLC., Chesterfield, MO (US)

( * ) Notice: Subject to any disclaimer, the term of this patent is extended or adjusted under 35 U.S.C. 154(b) by 374 days.

(21) Appl. No.: 12/181,640

(22) Filed: Jul. 29, 2008

(65) Prior Publication Data
US 2010/0024807 A1  Feb. 4, 2010

(30) Foreign Application Priority Data

Jul. 24, 2008 (CA) .................................. 2638159

(51) Int. Cl.
| C13K 1/02 | (2006.01) |
| C13K 13/00 | (2006.01) |
| B01F 15/00 | (2006.01) |
| C12P 7/10 | (2006.01) |

(52) U.S. Cl.
CPC . *C13K 1/02* (2013.01); *C13K 13/00* (2013.01); *B01F 15/0024* (2013.01); *C12P 7/10* (2013.01); *C12P 2203/00* (2013.01); *C12P 2201/00* (2013.01); *Y02E 50/16* (2013.01)
USPC ............................... 127/1; 127/37; 366/151.1

(58) Field of Classification Search
CPC ..................... B01F 2215/0013; B01F 15/0024; B01F 15/00233; Y02E 50/16; C08B 30/16; C13K 13/00; C13K 1/02; C12P 7/10; C12P 2201/00; C12P 2203/00
USPC ................ 127/1, 31, 34, 36, 67; 34/526–528; 162/237, 238, 21, 22; 366/151.1, 366/152.1, 144, 145, 149, 147, 101, 107; 536/124
See application file for complete search history.

(56) References Cited

U.S. PATENT DOCUMENTS

| 319,299 A | 6/1885 | Morgan |
| 459,113 A | 9/1897 | Rymal |

(Continued)

FOREIGN PATENT DOCUMENTS

| CA | 1070537 | 1/1980 |
| CA | 1096374 B | 2/1981 |

(Continued)

OTHER PUBLICATIONS

Schell et al., Dilute-sulfuric acid pretreatment of corn stover in pilot-scale reactor, 2003, Humana Press Inc., vol. 105, No. 1-3, pp. 69-85.*

(Continued)

*Primary Examiner* — David C Mellon
(74) *Attorney, Agent, or Firm* — Armstrong Teasdale LLP

(57) ABSTRACT

A method and apparatus for treating a cellulosic feedstock, such as for subsequent ethanol production, are disclosed. The method comprises determining an initial moisture content of the cellulosic feedstock and adding an amount of moisture to the cellulosic feedstock to obtain a predetermined moisture content of the cellulosic feedstock, wherein the cellulosic feedstock may subsequently be subjected to hydrolysis. The apparatus comprises a moisture sensor that provides an initial moisture content reading of the cellulosic feedstock, and a weight sensor providing the weight of the cellulosic feedstock. A processor is configured to determine an amount of moisture to be added to the cellulosic feedstock based on the weight and the initial moisture content of the cellulosic feedstock to obtain treated cellulosic feedstock having a predetermined moisture content.

14 Claims, 8 Drawing Sheets

(56) References Cited

U.S. PATENT DOCUMENTS

| | | | |
|---|---|---|---|
| 1,073,425 A | 9/1913 | Lambert | |
| 1,106,736 A | 8/1914 | Schuller | |
| 1,173,825 A | 2/1916 | McWallen | |
| 1,190,923 A | 7/1916 | Lindquist | |
| 1,247,153 A | 11/1917 | Roberts | |
| 1,560,855 A | 11/1925 | Queneau | |
| 1,824,221 A | 9/1931 | Mason | |
| 2,080,327 A | 5/1937 | McKinnis | |
| 2,086,701 A * | 7/1937 | Dreyfus | 127/37 |
| 2,263,608 A | 11/1941 | Brown | |
| 2,333,739 A | 11/1943 | Puckett | |
| 2,541,058 A | 2/1951 | Heritage et al. | |
| 2,541,059 A | 2/1951 | Heritage et al. | |
| 2,541,127 A | 2/1951 | Van Beckum | |
| 2,570,042 A | 10/1951 | West | |
| 2,595,827 A | 5/1952 | Boruff et al. | |
| 2,615,883 A | 10/1952 | Sweeney et al. | |
| 2,697,703 A | 12/1954 | Heritage et al. | |
| 2,758,031 A | 8/1956 | Ozai-Durrani | |
| 3,017,404 A | 1/1962 | Ball | |
| 3,109,560 A | 11/1963 | Rosenleaf | |
| 3,223,697 A | 12/1965 | Ball et al. | |
| 3,357,437 A | 12/1967 | Maguire | |
| 3,383,277 A | 5/1968 | Gordon et al. | |
| 3,407,943 A | 10/1968 | Douglass, Jr. | |
| 3,572,593 A | 3/1971 | Guarisco | |
| 3,617,433 A | 11/1971 | Sutherland | |
| 3,640,509 A | 2/1972 | Inamura et al. | |
| 3,743,572 A | 7/1973 | Richter et al. | |
| 3,817,826 A | 6/1974 | Hoye | |
| 3,964,874 A | 6/1976 | Maruko et al. | |
| 3,964,880 A | 6/1976 | Siegrist | |
| 4,023,982 A | 5/1977 | Knaugh | |
| 4,055,673 A * | 10/1977 | Mueller et al. | 426/231 |
| 4,062,304 A | 12/1977 | Herbold et al. | |
| 4,119,025 A | 10/1978 | Brown | |
| 4,136,207 A | 1/1979 | Bender | |
| 4,160,695 A | 7/1979 | Dietrichs et al. | |
| 4,181,796 A | 1/1980 | Dietrichs et al. | |
| 4,186,658 A | 2/1980 | Brown | |
| 4,196,827 A | 4/1980 | Leafdale | |
| 4,200,692 A | 4/1980 | Puls et al. | |
| 4,211,163 A | 7/1980 | Brown et al. | |
| 4,237,226 A | 12/1980 | Grethlein | |
| 4,281,934 A | 8/1981 | Krause | |
| 4,286,884 A | 9/1981 | Retrum | |
| 4,296,864 A | 10/1981 | Misaka et al. | |
| 4,316,748 A | 2/1982 | Rugg et al. | |
| 4,331,447 A | 5/1982 | Kamada et al. | |
| 4,341,353 A | 7/1982 | Hamilton et al. | |
| 4,364,667 A | 12/1982 | Reiner | |
| 4,412,485 A | 11/1983 | Brown | |
| 4,427,453 A * | 1/1984 | Reitter | 127/1 |
| 4,432,805 A | 2/1984 | Nuuttila et al. | |
| 4,436,586 A | 3/1984 | Elmore | |
| 4,451,567 A | 5/1984 | Ishibashi et al. | |
| 4,461,648 A | 7/1984 | Foody | |
| 4,470,851 A | 9/1984 | Paszner et al. | |
| 4,483,625 A | 11/1984 | Fisher et al. | |
| 4,511,433 A | 4/1985 | Tournier et al. | |
| 4,584,057 A | 4/1986 | Rowe et al. | |
| 4,600,590 A | 7/1986 | Dale | |
| 4,615,742 A | 10/1986 | Wright | |
| 4,645,541 A | 2/1987 | Delong | |
| 4,667,373 A | 5/1987 | Roder | |
| 4,670,944 A | 6/1987 | Thrash | |
| 4,676,363 A | 6/1987 | Buchmuller et al. | |
| 4,746,404 A | 5/1988 | Laakso | |
| 4,751,034 A | 6/1988 | Delong et al. | |
| 4,752,579 A | 6/1988 | Arena et al. | |
| 4,764,596 A | 8/1988 | Lora et al. | |
| 4,775,239 A | 10/1988 | Martinek et al. | |
| 4,798,651 A | 1/1989 | Kokta | |
| 4,867,846 A | 9/1989 | Fleck | |
| 4,869,786 A | 9/1989 | Hanke | |
| 4,908,098 A | 3/1990 | Delong et al. | |
| 4,908,099 A | 3/1990 | Delong | |
| 4,911,558 A | 3/1990 | Teske | |
| 4,947,743 A | 8/1990 | Brown et al. | |
| 4,966,650 A | 10/1990 | Delong et al. | |
| 4,997,488 A | 3/1991 | Gould et al. | |
| 5,012,731 A | 5/1991 | Maisonneuve | |
| 5,023,097 A | 6/1991 | Tyson et al. | |
| 5,034,099 A | 7/1991 | Nilsson | |
| 5,047,332 A | 9/1991 | Chahal | |
| 5,052,874 A | 10/1991 | Johanson | |
| 5,100,066 A | 3/1992 | Frei | |
| 5,114,488 A | 5/1992 | Huber et al. | |
| 5,122,228 A | 6/1992 | Bouchette et al. | |
| 5,135,861 A | 8/1992 | Pavilon | |
| 5,176,295 A | 1/1993 | Stefanik | |
| 5,181,804 A | 1/1993 | Wysong et al. | |
| 5,188,298 A | 2/1993 | Gerber | |
| 5,198,074 A | 3/1993 | Villavicencio et al. | |
| 5,221,357 A | 6/1993 | Brink | |
| 5,338,366 A * | 8/1994 | Grace et al. | 127/37 |
| 5,348,871 A | 9/1994 | Scott et al. | |
| 5,366,558 A | 11/1994 | Brink | |
| 5,411,594 A | 5/1995 | Brelsford | |
| 5,424,417 A | 6/1995 | Torget et al. | |
| 5,487,989 A | 1/1996 | Fowler et al. | |
| 5,503,996 A | 4/1996 | Torget et al. | |
| 5,504,259 A | 4/1996 | Diebold et al. | |
| 5,536,325 A | 7/1996 | Brink | |
| 5,571,703 A | 11/1996 | Chieffalo et al. | |
| 5,597,714 A | 1/1997 | Farone et al. | |
| 5,611,930 A | 3/1997 | Nguyen et al. | |
| 5,628,830 A | 5/1997 | Brink | |
| 5,677,154 A | 10/1997 | Van Draanen et al. | |
| 5,705,216 A | 1/1998 | Tyson | |
| 5,705,369 A | 1/1998 | Torget et al. | |
| 5,730,837 A | 3/1998 | Black et al. | |
| 5,733,758 A | 3/1998 | Nguyen | |
| 5,735,916 A | 4/1998 | Lucas et al. | |
| 5,791,779 A | 8/1998 | Smith | |
| 5,843,760 A | 12/1998 | Zhang et al. | |
| 5,863,389 A | 1/1999 | White et al. | |
| 5,916,780 A | 6/1999 | Foody et al. | |
| 5,932,452 A | 8/1999 | Mustranta et al. | |
| 6,022,419 A | 2/2000 | Torget et al. | |
| 6,063,204 A | 5/2000 | Hester et al. | |
| 6,090,595 A | 7/2000 | Foody et al. | |
| 6,199,299 B1 | 3/2001 | Prough et al. | |
| 6,228,177 B1 | 5/2001 | Torget | |
| 6,330,767 B1 | 12/2001 | Carr et al. | |
| 6,336,573 B1 | 1/2002 | Johanson | |
| 6,409,841 B1 | 6/2002 | Lombard | |
| 6,419,788 B1 | 7/2002 | Wingerson | |
| 6,423,145 B1 | 7/2002 | Nguyen et al. | |
| 6,498,029 B2 | 12/2002 | Keller, Jr. et al. | |
| 6,557,267 B2 | 5/2003 | Wanger | |
| 6,569,653 B1 | 5/2003 | Alard et al. | |
| 6,572,734 B2 | 6/2003 | Baker | |
| 6,620,292 B2 | 9/2003 | Wingerson | |
| 6,660,506 B2 | 12/2003 | Nguyen et al. | |
| 6,737,258 B2 | 5/2004 | Hames et al. | |
| 6,743,928 B1 | 6/2004 | Zeitsch | |
| 6,908,995 B2 | 6/2005 | Blount | |
| 6,927,048 B2 | 8/2005 | Verser et al. | |
| 7,109,005 B2 | 9/2006 | Eroma et al. | |
| 7,178,698 B2 | 2/2007 | Forslund et al. | |
| 7,198,925 B2 | 4/2007 | Foody | |
| 7,238,242 B2 | 7/2007 | Pinatti et al. | |
| 7,396,434 B2 | 7/2008 | Rodriguez Rivera et al. | |
| 7,445,691 B2 | 11/2008 | Snekkenes et al. | |
| 7,461,591 B2 | 12/2008 | Babbini | |
| 7,494,675 B2 | 2/2009 | Abbas et al. | |
| 7,503,981 B2 | 3/2009 | Wyman et al. | |
| 7,875,444 B2 | 1/2011 | Yang et al. | |
| 7,901,511 B2 | 3/2011 | Griffin et al. | |
| 7,937,851 B2 | 5/2011 | Rajagopalan et al. | |
| 7,993,463 B2 | 8/2011 | Griffin et al. | |
| 8,051,986 B2 | 11/2011 | Lees | |
| 8,053,566 B2 | 11/2011 | Belanger et al. | |

(56) References Cited

U.S. PATENT DOCUMENTS

| | | |
|---|---|---|
| 8,193,395 B2 | 6/2012 | Fenton et al. |
| 8,449,680 B2 | 5/2013 | Burke et al. |
| 2002/0003032 A1 | 1/2002 | Nay et al. |
| 2002/0164731 A1 | 11/2002 | Eroma et al. |
| 2003/0089465 A1 | 5/2003 | Schaible et al. |
| 2004/0121436 A1 | 6/2004 | Blount |
| 2004/0154760 A1 | 8/2004 | Dean |
| 2004/0171136 A1 | 9/2004 | Holtzapple et al. |
| 2004/0231661 A1 | 11/2004 | Griffin et al. |
| 2004/0231811 A1 | 11/2004 | Engstrand et al. |
| 2005/0269048 A1 | 12/2005 | Rodriguez et al. |
| 2006/0088922 A1 | 4/2006 | Yang et al. |
| 2006/0163118 A1 | 7/2006 | Kelsey et al. |
| 2006/0169430 A1 | 8/2006 | Tarasenko |
| 2006/0188965 A1 | 8/2006 | Wyman et al. |
| 2006/0233864 A1 | 10/2006 | Power |
| 2006/0272518 A1 | 12/2006 | Babbini |
| 2006/0275895 A1 | 12/2006 | Jensen et al. |
| 2007/0037267 A1 | 2/2007 | Lewis et al. |
| 2007/0148751 A1 | 6/2007 | Griffin et al. |
| 2007/0209974 A1 | 9/2007 | Lees |
| 2007/0215300 A1 | 9/2007 | Upfal et al. |
| 2007/0218530 A1 | 9/2007 | Duck et al. |
| 2007/0227063 A1 | 10/2007 | Dale et al. |
| 2008/0026431 A1 | 1/2008 | Saito et al. |
| 2008/0038784 A1 | 2/2008 | D'Arnaud-Taylor |
| 2008/0227161 A1 | 9/2008 | Levie et al. |
| 2009/0029432 A1 | 1/2009 | Abbas et al. |
| 2009/0062516 A1 | 3/2009 | Belanger et al. |
| 2009/0069550 A1 | 3/2009 | Belanger et al. |
| 2009/0098616 A1 | 4/2009 | Burke et al. |
| 2009/0098617 A1 | 4/2009 | Burke et al. |
| 2009/0240088 A1 | 9/2009 | Fenton et al. |
| 2009/0246848 A1 | 10/2009 | Noel |
| 2010/0024806 A1 | 2/2010 | Burke et al. |
| 2010/0024807 A1 | 2/2010 | Burke et al. |
| 2010/0024808 A1 | 2/2010 | Burke et al. |
| 2010/0024809 A1 | 2/2010 | Burke et al. |
| 2010/0028089 A1 | 2/2010 | Burke et al. |
| 2010/0124583 A1 | 5/2010 | Medoff |
| 2010/0186735 A1 | 7/2010 | Burke et al. |
| 2010/0186736 A1 | 7/2010 | Burke et al. |
| 2011/0011391 A1 | 1/2011 | Burke |
| 2012/0111321 A1 | 5/2012 | Nguyen et al. |

FOREIGN PATENT DOCUMENTS

| | | |
|---|---|---|
| CA | 1147105 A | 5/1983 |
| CA | 1173825 A1 | 9/1984 |
| CA | 1190923 A1 | 7/1985 |
| CA | 1267407 | 3/1990 |
| CA | 1287705 | 8/1991 |
| CA | 2037275 A1 | 8/1992 |
| CA | 1322366 C | 9/1993 |
| CA | 2063547 A1 | 9/1993 |
| CA | 2065939 A1 | 10/1993 |
| CA | 2339002 A1 | 7/1999 |
| CA | 2638150 A1 | 1/2010 |
| CA | 2638159 A1 | 1/2010 |
| EP | 0487793 A1 | 6/1992 |
| EP | 0884391 B1 | 1/2002 |
| EP | 1316620 A2 | 6/2003 |
| EP | 1036236 | 7/2003 |
| FR | 777824 | 3/1935 |
| GB | 892506 | 3/1962 |
| GB | 1043460 A | 9/1966 |
| WO | 9213849 A1 | 8/1992 |
| WO | 2005079190 A2 | 9/1995 |
| WO | 9640970 A1 | 12/1996 |
| WO | 9732073 A1 | 9/1997 |
| WO | 0238787 A2 | 5/2002 |
| WO | 2004018645 A2 | 3/2004 |
| WO | 2004081193 A2 | 9/2004 |
| WO | 2004106624 A1 | 12/2004 |
| WO | 2005118165 A1 | 12/2005 |
| WO | 2006017655 A3 | 2/2006 |
| WO | 2006034591 A1 | 4/2006 |
| WO | 2006055362 A1 | 5/2006 |
| WO | 2006063467 A1 | 6/2006 |
| WO | 2007009463 A2 | 1/2007 |
| WO | 2007064296 A1 | 6/2007 |
| WO | 2007065241 A1 | 6/2007 |
| WO | 2007111605 A1 | 10/2007 |
| WO | 2008086115 A2 | 7/2008 |
| WO | 2008144903 A1 | 12/2008 |
| WO | 2009012779 A2 | 1/2009 |
| WO | 2009018469 A1 | 2/2009 |
| WO | 2009089439 A1 | 7/2009 |
| WO | 2010006840 A2 | 1/2010 |
| WO | 2010009547 A1 | 1/2010 |
| WO | 2010009548 A1 | 1/2010 |
| WO | 2010009549 A1 | 1/2010 |
| WO | 2010009550 A1 | 1/2010 |
| WO | 2010009551 A1 | 1/2010 |
| WO | 2010083600 A1 | 7/2010 |
| WO | 2010083601 A1 | 7/2010 |
| WO | 2011028554 A1 | 3/2011 |

OTHER PUBLICATIONS

International Search Report received on the corresponding international application No. PCT/CA2009/001035, dated Nov. 5, 2009.

Brownell et al.: "Steam-Explosion Pretreatment of Wood: Effect of Chip Size, Acid, Moisture Content, and Pressure Drop", Biotechnology and Bioengineering, vol. 28., pp. 792-801, (1986), p. 792, col. 2.

Cullis et al.: "Effect of Initial Moisture Content and Chip Size on the Bioconversion Efficiency of Softwood Lignocellulosics", Biotechnology and Bioengineering, vol. 85, No. 4, pp. 413-421, (2004), Abstract.

Duff et al.: "Bioconversion of forest products industry waste cellulosics to fuel ethanol: A review". Bioresource Technology, vol. 55, pp. 1-33, (1996).

International Search Report received on the corresponding international application No. PCT/CA2009/001032, dated Oct. 27, 2009.

Written Opinion of the International Searching Authority, dated Oct. 8, 2010, corresponding to International application No. PCT/CA2010/001091.

PCT International Search Report, dated Oct. 8, 2012, corresponding to International application No. PCT/CA2010/001091.

Office Action on co-pending Canadian Application 2,638,152 dated Feb. 8, 2011.

International Search Report and Written Opinion received on the corresponding international application No. PCT/CA2009/001033, mailed on Oct. 30, 2009.

Abengoa Bioenergy New Technologies Inc. f/k/a *Abengoa Bioenergy R&D, Inc.* v. *Mascoma Corporation*; Notice of Arbitration and Statement of Claim, submitted to American Arbitration Association Commercial Arbitration Tribunal on Nov. 2, 2011.

Q.A. Nguyen et al., "NREL/DOE Ethanol Pilot-Plant: Current Status and Capabilities" (1996) 58 Bioresource Technology 189.

R.P. Overend & E. Chornet, "Fractionation of lignocellulosics by steam-aqueous pretreatments" (1987) 321 Phil. Trans. R. Soc. Lond. A. 523.

D. Ballerini et al., "Ethanol Production from Lignocellulosics: Large Scale Experimentation and Economics" (1994) 50 Biousource Technology 17.

K.M.F. Kazi, P. Jollez, & E. Chornet, "Preimpregnation: An Important Step for Biomass Refining Processes" (1998) 15:2 Biomass and Bioenergy 125.

M.P. Tucker et al., "Comparison of Yellow Poplar Pretreatment Between NREL Digester and Sunds Hydrolyzer" (1998) 70-72 Applied Biochemistry and Biotechnology 25.

Charles E. Wyman et al., "Comparative Sugar Recovery Data from Laboratory Scale Application of Leading Pretreatment Technologies to Corn Stover" (2005) 96 Bioresource Technology 2026.

Charles E. Wyman et al., "Coordinated Development of Leading Biomass Pretreatment Technologies" (2005) 96 Bioresource Technology 1959.

(56) References Cited

OTHER PUBLICATIONS

Nathan Mosier et al., "Features of Promising Technologies for Pretreatment of Lignocellulosic Biomass" (2005) 96 Biosource Technology 673.

Tim Eggeman & Richard T. Elander, "Process and Economics Analysis of Pretreatment Technologies" (2005) 96 Bioresource Technology 2019.

Abengoa Bioenergy, Press Release, "Abengoa Bionergy Awarded DOE Financial Assistance Agreement" (Feb. 28, 2007), online: Abongoa Bioenergy <http://www.abengoabioenergy.es/corp/web/en/acerca_de/sala_de_prensa/historico/2007/20070228_noticias.html#>.

Outputs from the EPOBIO Workshop, Greece, "Products from Plants—From Crops and Forests to Zero Waste Biorefineries" (May 15-17, 2007).

Abengoa Bioenergy, Press Release, "Abengoa Bionergy Opens Pilot Plant for the Energy of the Future" (Oct. 15, 2007), online: Abengoa Bioenergy <http://www.abengoabioenergy.es/corp/web/en/acerca_de/sala_de_prensa/historico/2007/20071015_noticias.html#>.

Merrick & Company, Final Report of Jun. 14, 1999, "Softwood Biomass to Ethanol Feasibility Study" (Aug. 2004) Subcontractor Report published by National Renewable Energy Laboratory.

Merrick & Company, Final Report of Jan. 2000, "Building a Bridge to the Corn Ethanol Industry. Corn Stover to Ethanol at High Plains Corporation's York, Nebraska Co-Located Plant site".

Melvin P. Tucker et al., "Conversion of Distiller's Grain into Fuel Alcohol and a Higher-Value Animal Feed by Dilute-Acid Pretreament" (2004) 113-116 Applied Biochemistry and Biotechnology 1139.

Melvin P. Tucker et al., "Effects of Temperature and Moisture on Dilute-Acid Steam Explosion Pretreatment of Corn Stover and Cellulase Enzyme Digestibility" (2003) 105-108 Applied Biochemistry and Biotechnology 165.

Kyoung Heon Kim et al., "Continuous Countercurrent Extraction of Hemicellulose from Pretreated Wood Residues" (2001) 91-93 Applied Biochemistry and Biotechnology 253.

Quang A. Nguyen et al., "Two-Stage Diute-Acid Pretreatment of Softwoods" (2000) 84-86 Applied Biochemistry and Biotechnology 561.

Daniel J. Schell et al., "Dilute-Sulfuric Acid Pretreatment of Corn Stover in Pilot-Scale Reactor" (2003) 105-108 Applied Biochemistry and Biotechnology 69.

Q.A. Nguyen & J.N. Saddler, "An Integrated Model for the Technical and Economic Evaluation of an Enzymatic Biomass Conversion Process" (1991) 35 Bioresource and Technology 275.

Q.A. Nguyen et al., "Dilute Acid Pretreatment of Softwoods", Scientific Note, (1998) 70-72 Applied Biochemistry and Biotechnology 77.

Q.A. Nguyen et al., "Dilute Acid Hydrolysis of Softwoods", Scientific Note, (1999) 77-79 Applied Biochemistry and Biotechnology 133.

Raphael Katzen & Donald F. Othmer, "Wood Hydrolysis. A Continuous Process" (1942) 34 Industrial and Engineering Chemistry 314.

"Transactions of the Institution of Chemical Engineers" (1993) 11 Institution of Chemical Engineers, London, the United Kingdom.

Diane Knappert, Hans Grethlein & Alvin Converse, "Partial Acid Hydrolysis of Cellulosic Materials as a Pretreatment for Enzymatic Hydrolysis" (1980) 22 Biotechnology and Bioengineering 1449.

Sung Bae Kim & Y.Y. Lee, "Diffusion of Sulfuric Acid within Lignocellulosic Biomass Particles and its Impact on Dilute-Acid Pretreatment" (2002) 83 Bioresource Technology 165.

Alan W. Roberts, "Design Considerations and Performance Evaluation of Screw Conveyors", online: The South African Institute of Materials Handling <http://www.saimh.co.za/beltcon/beltcon11/beltcon1114.htm>.

National Renewable Energy Laboratory, "Process Design and Cost Estimate of Critical Equipment in the Biomass to Ethanol Process. Acid Hydrolysis Reactors Batch Systems", Report (Seattle, Washington: Harris Group Inc., 2001).

Osamu Kitani & Carl W.. Hall, eds., "Biomass Handbook" 470-474 (Gordon and Breach Science Publishers: New York).

Buell Classifier Fisher-Klosterman, Leaflet, "Operation Principles and Efficiency".

Process Sensors Corporation, "On-Line Moisture Measurement and Control Manufacturing Industries Worldwide", Product Information, online: Process Sensors Corporation <http://processsensors.com/index.html? gclid=CKT27fXvJ0CFREWagodclkUcw>.

Roger M. Rowell, Raymond A. Young, & Judith K. Rowell, eds., Paper and Composites from Agro-Based Resources (Lewis Publishers).

G.H.Emert et al., "Gasohol/Biomass Developments: Economic Update of the Gulf Cellulose Alcohol Process" (Sep. 1980) Chemical Engineering Progress 47.

Ron Kotrba, "The Project of a Lifetime" (Feb. 2006), Ethanol Producer Magazine.

National Renewable Energy Laboratory, "Research Advances: NREL Leads the Way. Cellulosic Ethanol", Brochure, (Mar. 2007), online: National Renewable Energy Laboratory <http://www.nrel.gov/biomass/pdfs/40742.pdf>.

National Renewable Energy Laboratory, Fact Sheet, "Clean Cities: Ethanol Basics" (Oct. 2008), online: U.S. Department of Energy <www.ardc.energy.gov/afdc/pdfs/43835.pdf>.

Brent D. Yacobucci, "Fuel Ethanol: Background and Public Policy Issues", (Mar. 3, 2006), CRS Report for Congress, online: U.S. Department of State, Foreign Press Centre <fpc.state.gov/documents/organization/62837.pdf>.

U.S. Department of Energy, Energy Efficiency & Renewable Energy, Alternative Fuels & Advanced Vehicles Data Center, Article, "Ethanol Market Penetration", online: U.S. Department of Energy <http://www.afdc.energy.gov/afdc/ethanol/market.html>.

Kenneth W.Britt, ed., "Handbook of Pulp and Paper Technology", 2nd. ed. (New York: Van Nostrand Reinhold Company).

A. Aden et al., "Lignocellulosic Biomass to Ethanol Process Design and Economics Utilizing Co-Current Dilute Acid Prehydrolysis and Enzymatic Hydrolysis for Corn Stover", (Jun. 2002), Technical Report published by National Renewable Energy Laboratory.

U.S. Department of Energy Office of Science, Genomics Science Program, "Fuel Ethanol Production", online: U.S. Department of Energy Office of Science <http://genomicscience.energy.gov/biofuels/ethanolproduction.shtml>.

Metso Automation, Metso Automation's Newsletter for Neles and Jamesbury products, "Biofuels—a growth market for Metso", (Summer 2008), online: Metso <http://valveproducts.metso.com/metsoautomation/DocDB/catalogs/catalog.taf?pg_parent=397>.

SunOpta Inc., News Release, "SunOpta Announces Sale of Cellulosic Ethanol Facility to China Resources Alcohol Corporation", (Jun. 23, 2006), online: SunOpta Inc. <http://investor.sunopta.com/releasedetail.cfm?ReleaseID=287111>.

Ralph P. Overend, Slideshow, "The Lignocellulosic bottleneck: material properties, architecture and pretreatment".

Robert Wooley et al., "Lignocellulosic Biomass to Ethanol Process Design and Economics Utilizing Co-Current Dilute Acid Prehydrolysis and Enzymatic Hydrolysis Current and Futuristic Scenarios", (Jul. 1999), National Renewable Energy Laborator. Technical Report.

Nathan S. Masier, "Cellulosic Ethanol—Biofuel Beyond Corn" Bio Energy, Purdue University.

U.S Securities and Exchange Commission, "Annual Report Under Section 13 or 15(d) of the Securities Exchange Act of 1934", for Bluefire Ethanol Fuels, Inc. Signed on Feb. 28, 2008.

U.S Securities and Exchange Commission, "Annual Report Under Section 1 or (15)d of the Securities Exchange Act of 1934", for CleanTech Biofuels, Inc. Signed on Mar. 28, 2008.

Liu, H., et al., "Lignin-Metal Complexation to Eliminate Nonproductive Enzyme Adsorption by Lignin in Unwashed Lignocellulosic Substrates," 2010, 32nd Symposium on Biotechnology for Fuels and Chemicals, 28 pages.

Ohgren, K., et al., "High Temperature Enzymatic Prehydrolysis Prior to Simultaneous Saccharification and Fermentation of Steam Pretreated Corn Stover for Ethanol Production," 2007, Enzyme Microb Technol, 40/4:607-613.

(56) References Cited

OTHER PUBLICATIONS

Pan, X., et al., "Bioconversion of Hybrid Poplar to Ethanol and Co-Products Using an Organosolv Fractionation Process: Optimization of Process Yields," 2006, Biotech and Bioeng, 94/5:851-861.
PROPAX Yeast Propagation Technology, Product Brochure, Meura S.A., Edited 2009, 2 pages.
Ramsay, J.A., et al., "Biological Conversion of Hemicellulose to Propionic Acid," 1998, Enzyme Microb Technol, 22:292-295.
Schell, D.J., et al., "A Bioethanol Process Development Unit: Initial Operating Experiences and Results with a Corn Fiber Feedstock," 2004, Bioresource Technology, 91:179-188.
Sharma-Shivappa, R.R., et al, "Conversion of Cotton Wastes to Bioenergy and Value-Added Products," 2008, Transactions of the ASABE, 51/6:2239-2246.
SILWET L-77 Surfactant, Specimen Label, Helena Chemical Company, Copyright 2006, 2 pages.
Sluiter, A., et al., "Determination of Ash in Biomass, Laboratory Analytical Procedure (LAP)," NREL Technical Report, NREL/TP-510-42622, Jan. 2008, 8 pages.
Sluiter, A., et al., "Determination of Extractives in Biomass, Laboratory Analytical Procedure (LAP)," NREL Technical Report, NREL/TP-510-42619, Jan. 2008, 12 pages.
Sluiter, A., et al., "Determination of Structural Carbohydrates and Lignin in Biomass, Laboratory Analytical Procedure (LAP)," NREL Technical Report, NREL/TP-510-42618, Apr. 2008, 16 pages.
Sluiter, A., et al., "Determination of Sugars, Byproducts, and Degradation Products in Liquid Fraction Process Samples, Laboratory Analytical Procedure (LAP)," NREL Technical Report, NREL/TP-510-42623, Jan. 2008, 14 pages.
Sluiter, A., et al., "Determination of Total Solids in Biomass and Total Dissolved Solids in Liquid Process Samples, Laboratory Analytical Procedure (LAP)," NREL Technical Report, NREL/TP-510-42621, Mar. 2008, 9 pages.
Sun, L., "Silicon-Based Materials from Rice Husks and Their Applications," 2001, Ind Eng Chem Res, 40/25:5861-5877, Abstract Only, 1 page.
SUPERFRAC High Performance Trays, Product Brochure, Koch-Glitsch, Bulletin KGSF-1, Revised Mar. 2010, 16 pages.
Taherzadeh, M. J. et al., "Pretreatment of Lignocellulosic Wastes to Improve Ethanol and Biogas Production: A Review," 2008, Int. J. Mol. Sci., (9) 1621-1651.
Teleman, et al., "Progress-Curve Analysis Shows that Glucose Inhibits the Cellotriose Hydrosysis Catalysed by Cellobiohydrolase II from Trichoderma Reesi," 1995, European J Biochem, 231:250-258.
The Artisan Dualflo Tray, Product Brochure, Artisan Industries, Inc., Bulletin 9801, Edit Date Apr. 17, 2003, 2 pages.
Thomas, S., et al., "Biofuels Program C-Milestone Completion Report," FY02, DOE Biofuels Program, Report #373, 2002, 51 pages.
Thomas, S.R., "Corn Stover Feedstock Variability," 2005, Feedstock Area Stage Gate Review Meeting, 34 pages.
Thompson, D.N., et al., "Post-Harvest Processing Methods for Reduction of Silica and Alkali Metals in Wheat Straw," 2002, 24th Symposium on Biotechnology for Fuels and Chemicals, Poster #1-30, 21 pages.
Viamajala, S., et al., "Catalyst Transport in Corn Stover Internodes," 2005, Appl Biochem and Biotech, 129-132:509-527.
Weiss, N.D., et al., "Catalyst Impregnation for High Solids Biomass Pretreatment," 2008, AIChE Annual Meeting, 24 pages.
Yang, B., et al., "Chapter 6. Unconventional Relationships for Hemicellulose Hydrolysis and Subsequent Cellulose Digestion," 2004, Lignocellulose Biodegradation, ACS Symposium Series 889, American Chemical Society, pp. 100-125.
Zimbardi, F., et al., "Acid Impregnation and Steam Explosion of Corn Stover in Batch Processes," 2007, Ind Crops and Products, 26:195-206.
"Biofuels Pilot Plant Under Way," Newsbriefs, Chemical Week, Oct. 13/20, 2008, p. 4.
"Easy Steps for Optimal Yeast Rehydration," Laboratory Protocol, Scott Laboratories, Petaluma CA, 1 page.
"Enzyme Sugar-Ethanol Platform Project," NREL, U.S. Dept. of Energy by Midwest Research Institute, Battelle, Bechtel, 47 pages.
"Ethanol Annual Report FY 1990", SERI, TP-231/3996, Prepared for the U.S. DOE, Jan. 1991, Contract No. DE-AC02-83CH10093, Texeira, R.H. And Goodman, B.J., editors, 344 pages.
"Lessons Learned from Existing Biomass Power Plants," Feb. 2000, NREL/SR-570-26946, G. Wiltsee, Appel Consultants, Inc., Valencia, CA, 149 pages.
"Process Design and Cost Estimate of Critical Equipment in the Biomass to Ethanol Process, Report 99-10600/17 Continuous Acid Hydrolysis Reactor," Jan. 22, 2011 Rev WEB, Subcontract ACO-9-29067-01, National Renewable Energy Laboratory, Golden, CA, Harris Group Inc., Seattle, WA, 14 pages.
"Types of Lignin and Their Properties," 2001, Information Service from the Lignin Institute, 9/1:4 pages, www.lignin.org/01augdialogue.html.
Abstract of Chinese Patent Application CN 101310879 A, 2008, Institute of Process Engineering, Chinese Academy of Sciences.
ACTIVATOR 90, Product Brochure, 2009, Loveland Products Inc., No. 6566_05/09, 1 page.
Al-Halaly, A.S.M., "A Study of Some Anatomical Chemical Properties and Specific Gravity of Casuarina Equisetifolia Forst. Wood Grown in Iraq," 1985, AGRIS Record No. IQ8500239, Abstract, 1 page.
AMISTCO Tower Trays, Product Brochure, Amistco Separation Products, Inc., 8 pages.
Antongiovanni, M., et al., "Variability in Chemical Composition of Straws," 1991, CIHEAM—Options Mediterraneennes, Serie Seminaires, 16:49-53.
Awafo, V.A., et al., "Evaluation of Combination Treatments of Sodium Hydroxide and Steam Explosion for the Production of Cellulase-Systems by Two T. reesei Mutants Under Solid-State Fermentation Conditions," 2000, Bioresource Tech, 73:235-245.
Azadbakht, M., et al., "Preparation of Lignin From Wood Dust as Vanillin Source and Comparison of Different Extraction Methods," Oct. 2004, Int J of Biol and Biotech, 1/4:535-537, Abstract Only, 1 page.
Bakker, R. R., et al., "Biofuel Production from Acid-Impregnated Willow and Switchgrass," 2nd World Conference on Biomass for Energy, Industry and Climate Protection, May 10-14, 2004, Rome, Italy, pp. 1467-1470.
Bigelow, M., et al., "Cellulase Production on Bagasse Pretreated with Hot Water," 2002, App Biochem and Biotech, 98-100:921-934.
Coons, R., "DSM Launches Cellulosic Biofuel Project," Oct. 27, 2008, Chemical Week, 170/33:9.
Coons, R., "Novozymes Ramps Up Focus on Second-Generation Biofuels," Oct. 27, 2008, Chemical Week, 170/33:30.
Cunningham, R.L., et al., "Improved Hemicellulose Recovery From Wheat Straw," 1985, Biotech and Bioeng Symp No. 15, Seventh Symposium on Biotechnology for Fuels and Chemicals, pp. 17-26.
Dasari, R.K., et al., "The Effect of Particle Size on Hydrolysis Reaction Rates and Rheological Properties in Cellulosic Slurries," 2007, Appl Biochem and Biotech, Session 2, 137-140/1-2, 289-299, Abstract Only.
De Castro, F.B., "The Use of Steam Treatment to Upgrade Lignocellulosic Materials for Animal Feed," 1994, Thesis, University of Aberdeen, 214 pages.
Dowe, N., et al., "SSF Experimental Protocols-Lignocellulosic Biomass Hydrolysis and Fermentation, Laboratory Analytical Procedure (LAP)," Jan. 2008, NREL Technical Report, NREL/TP-510-42630, 19 pages.
Esteghlalian, A., et al., "Modeling and Optimization of the Dilute-Sulfuric-Acid Pretreatment of Corn Stover, Poplar and Switchgrass," 1997, Bioresource Technology, 59:129-136.
Fan, L.T., et al., "Evaluation of Pretreatments for Enzymatic Conversion of Agricultural Residues," 1981, Biotechnology & Bioengineering Symposium, 11:29-45 (Proceedings of the Third Symposium on Biotechnology in Energy Production and Conservation, Gatlinburg, TN, May 12-15, 1981).
Flexitray Valve Trays, Product Brochure, Koch-Glitsch, Bulletin FTCVT-01, Revised Mar. 2010, 12 pages.
Flint, S.I., et al., "Recovery of Lignin During Nonstarch Polysaccharide Analysis," 1992, Cereal Chem, 69/4:444-447.

(56) References Cited

OTHER PUBLICATIONS

Foody, P., "Optimization of Steam Explosion Pretreatment," 1980, Final Report to DOE, Report No. DOE/ET23050-1, Contract No. AC02-79ET23050, Bibliographic Citation, 1 page.

Fuel Ethanol Application Sheet, "CELLIC Ctec and Htec2—Enzymes for Hydrolysis of Lignocellulosic Materials," Novozymes A/S, Luna No. 2010-01668-01, 9 pages, 2010.

GEA Wiegand, GmbH, Process Engineering Division, "Bioethanol Technology", Ettlingen, Germany, Company Brochure, 16 pages.

Gea Wiegand, GmbH, Process Engineering Division, "Distillation Technology", Ettlingen, Germany, Company Brochure, 16 pages.

Ghose, T.K., "Measurement of Cellulase Activities," 1987, Pure and Appl. Chem., 59/2:257-268.

Grethlein, H.E., "Chemical Breakdown of Cellulosic Materials," 1978, J. Appl. Chem. Biotechnol. 28:296-308.

Grethlein, H.E., et al., "Common Aspects of Acid Prehydrolysis and Steam Explosion for Pretreating Wood," 1991, Bioresource Technology, 36:77-82.

Grohmann, K., et al., "Optimization of Dilute Acid Pretreatment of Biomass," Proceedings of the Seventh Symposium on Biotechnology for Fuels and Chemicals, May 14-17, 1986, 24 pages.

Hames, B., et al., "Determination of Protein Content in Biomass, Laboratory Analytical Procedure (LAP)," May 2008, NREL Technical Report, NREL/TP-510-42625, 8 pages.

Hames, B., et al., "Preparation of Samples for Compositional Analysis, Laboratory Analytical Procedure (LAP)," Aug. 2008, NREL Technical Report, NREL/TP-510-42620, 12 pages.

International Search Report and the Written Opinion issued in connection with PCT Application No. PCT/CA2009/001032, mailed on Oct. 27, 2009, 11 pages.

International Search Report and the Written Opinion issued in connection with PCT Application No. PCT/CA2009/001036, dated Nov. 13, 2009, 6 pages.

International Search Report and the Written Opinion issued in connection with PCT Application No. PCT/CA2010/000087, mailed on May 4, 2010, 10 pages.

International Search Report and the Written Opinion issued in connection with PCT Application No. PCT/CA2010/000088, mailed on May 14, 2010, 15 pages.

International Search Report issued in connection with PCT Application No. PCT/CA2010/000088, mailed as a corrected version on Jun. 17, 2010.

International Search Report and the Written Opinion issued in connection with PCT Application No. PCT/US2010/46561, dated Dec. 20, 2010, 16 pages.

International Search Report and the Written Opinion issued in PCT Application No. PCT/CA2009/001034, dated Oct. 20, 2009, 9 pages.

International Preliminary Report of Patentability issued in connection with International Application No. PCT/CA2009/001034, issued on Jan. 25, 2011.

International Search Report and the Written Opinion issued in PCT Application No. PCT/US2012/022552, dated May 15, 2012, 18 pages.

Juhasz, T., et al., "Characterization of Cellulases and Hemicellulases Produced by Trichoderma reesei on Various Carbon Sources," 2005, Process Biochem, 40:3519-3525.

Keller, F.A., et al., "Yeast Adaptation on Softwood Prehydrolysate," 1998, Appl Biochem and Biotech, 70-72:137-148.

Kolar, L., et al., "Agrochemical Value of Organic Matter of Fermenter Wastes in Biogas Production," 2008, Plant Soil Environ, 54/8:321-328.

Kumar, R., et al., "The Impact of Dilute Sulfuric Acid on the Selectivity of Xylooligomer Depolymerization to Monomers," 2008, Carbohydrate Res, 343:290-300.

Linde, M., et al., "Steam Pretreatment of Acid-Sprayed and Acid-Soaked Barley Straw for Production of Ethanol," 2006, Appl Biochem and Biotech, 129-132:546-562.

\* cited by examiner

METHOD AND APPARATUS FOR TREATING A CELLULOSIC FEEDSTOCK

FIELD

The invention relates to a method and apparatus for treating a cellulosic feedstock for subsequent ethanol production. More specifically, the invention relates to a method and apparatus for preparing the cellulosic feedstock for the subsequent production of a fermentable sugar stream from the cellulose and hemicellulose in the cellulosic feedstock.

BACKGROUND

Several processes for the production of ethanol are known. Generally, the production of fuel ethanol involves the fermentation of sugars with yeast. Typically, the sugars are derived from grains, such as corn and wheat. The starches in the grains are subjected to enzymatic hydrolysis in order to produce the sugars, which are then subjected to fermentation to produce ethanol.

Plant materials are a significant source of fermentable sugars, such as glucose that can be transformed into biofuels. However, the sugars in plant materials are contained in long polymeric chains of cellulose and hemicellulose. Utilizing current fermentation processes, it is necessary to break down these polymeric chains into monomeric sugars, prior to the fermenting step.

Recently, processes have been developed for utilizing plant materials, such as corncobs, straw, and sawdust, to produce sugars for ethanol fermentation. Such processes typically comprise pre-treating the feedstock to increase the accessibility of the cellulose to hydrolysis enzymes, and subjecting the cellulose to cellulase enzyme systems to convert the cellulose into glucose.

Methods of converting plant biomass into fermentable sugars are known in the art and in general comprise two main steps: a pre-treatment step to activate the plant structure, and an enzymatic or chemical hydrolysis step to convert the polymeric chains of cellulose and hemicellulose into monomeric sugars. Several approaches have been used for the pre-treatment step, e.g., autohydrolysis, acid hydrolysis, ammonia activation, kraft pulping, organic solvent pulping, hot water pre-treatment, ammonia percolation, lime pre-treatment, caustic soda pulping, or alkali peroxide pre-treatment. Early pre-treatment steps included grinding or milling the feedstock into a powder, which was then mixed with water to form a slurry.

More recently, solvent based pre-treatments, alkali pre-treatments, and acidic pre-treatments have also been described. PCT publication WO/2007/009463 to Holm Christensen describes an alternate pre-treatment, which does not involve the addition of acids, bases, or other chemicals. This pre-treatment process involves soaking the cellulosic material in water, conveying the cellulosic material through a heated and pressurized reactor, and pressing the cellulosic material to produce a fiber fraction and a liquid fraction. During the soaking step, approximately 2.5-3.5 kg of liquid per 1 kg of fiber is added, and is removed again during pressing. The overall pre-treatment process can take about 27 minutes.

Each pre-treatment technology has a different mechanism of action on the plant structure, inducing either physical and/or chemical modifications. However, the main objective of the pre-treatment is to provide accessibility of the plant material to the enzymes.

SUMMARY

The commercial viability of a hydrolysis process is dependent on the character of the feedstock provided to the hydrolysis unit. Typically, this requires that a feedstock is activated such that a significant portion (e.g., greater then 75%) of the cellulose and hemicellulose of the feedstock is accessible to hydrolysis enzymes. If such an activated feedstock is provided to an enzymatic hydrolysis unit, then at least 60%, preferably more than 75% and more preferably over 90% of the cellulose and hemicelluloses may be converted to monomeric sugars. This sugar rich process stream may subsequently be subjected to fermentation to produce an alcohol stream. The alcohol stream from the fermentation stage (i.e., the raw alcohol stream) may have an ethanol content of about 3-22% v/v, preferably about 5-15% and more preferably more about 8-12%.

An activated feedstock for enzymatic hydrolysis is preferably prepared by autohydrolysis, which is preferably conducted in a steam explosion reactor also known as a hydrolyser (also known as a digester). Autohydrolysis is a process of breaking down hemicellulose and cellulose by exposure to high temperatures, steam and pressure. When performed in the presence of an added acid, the reaction is known as acid hydrolysis.

During autohydrolysis, the degree of polymerization of cellulose may be reduced from about 10,000 to about 1,500-1,000. This process is preferably carried out above the glass transition temperature of lignin (120-160° C.). Depending upon the severity of the reaction, degradation products may be produced, such as furfural, hydroxyl-methylfurfural, formic acid, levulinic acid and other organic compounds.

During a steam explosion treatment (more commonly called autohydrolysis if no externally added catalyst), a cellulosic feedstock is subjected to elevated temperature (e.g., 180° C. to 220° C.) and pressure (e.g., 131 psig to 322 psig) optionally in the presence of suitable chemicals (e.g., organic and/or inorganic acids, ammonia, caustic soda, sulfur dioxide, solvents etc.) in a pressurized vessel. Preferably, external chemical addition is not utilized, in which case, the only catalyst that may be present may be acetic acid that is generated in situ. The treated cellulosic feedstock is then released from the pressurized vessel such that the pressure is rapidly reduced (e.g., 1 second or less). The biomass may exit the hydrolyser into a reduced pressure, preferably atmospheric pressure and, more preferably into a vacuum. The rapid decrease in pressure results in the biomass separating into individual fibers or bundles of fibers. This step opens the fiber structure and increases the surface area. The lignin remains in the fiber along with cellulose and residual hemicellulose. Accordingly, the explosive release of pressure, combined with the high temperature and pressure treatment results in the physicochemical modification of the cellulosic feedstock that is then suitable for feeding to an enzymatic hydrolysis unit.

In order for the steam explosion process to be able to produce an activated feedstock that is capable of producing such a sugar rich process stream, the temperature and moisture level of the cellulosic feedstock that is fed to a steam explosion reactor preferably is relatively uniform and preferably has a temperature from about 50 to about 70° C. and, more preferably 50-65° C., and a moisture content from about 30 to 60 wt % (preferably 45 to about 55 wt %).

Without being limited by theory, it is believed that an unexpected increase in the conversion of the feedstock to fermentable sugars may be achieved if the moisture content of the feedstock fed to the steam explosion reactor is lower, provided that sufficient water is present for hydrolyzing and/or activating the feedstock. If the feedstock is too dry, then there may be insufficient water molecules present in the fiber and hence not all of the feedstock will be hydrolyzed and/or activated (i.e., the hydrolysis reaction/activation will not occur at all possible sites). Accordingly, it might be presumed that a substantial excess of water should be used to ensure water molecules are available at each hydrolysis/activation-site. Surprisingly, it has been determined that if the cellulosic feedstock that is fed to a steam explosion reactor has an excess of moisture then a smaller percentage of the available sites of the feedstock are activated and/or hydrolyzed than would be expected. It is believed that this is due to the high moisture content acting as a barrier to heat transfer through the fiber structure. The external fiber reaches the process temperature far in advance to the internal fiber, hence resulting in very uneven heat transfer and the resulting uneven autohydrolysis reaction. Further, during the autohydrolysis process additional water may be provided to the process by way of direct injected steam in order to raise the fiber temperature from the inlet temperature to the outlet temperature of the reactor. If the inlet moisture content of the fiber is at saturation, then the additional water will be free water in the autohydrolysis reactor resulting in washing of the soluble hemicellulose from the fiber and causing subsequent accumulation of hemicellulose within the reactor. Over time, the accumulated hemicellulose will tend to break down to inhibitor compounds and deposit degraded sugars on the internal components of the reactor. These deposits become an obstruction to the flow of the biomass.

It has also been determined that if the cellulosic feedstock is fed to a hydrolyzer at a temperature that is too high, then some percentage of the hemicellulose sugars will be degraded to inhibitory compounds prior to starting the autohydrolysis reaction and further amounts during the autohydrolysis reaction itself. Conversely, if the fiber is too cold entering the autohydrolysis reactor, the first one third to one half of the reactor vessel may act as a preheating device rather than as an autohydrolysis reactor, resulting in incomplete autohydrolysis. Accordingly, it is preferred to have very consistent fiber temperature year round as well as from night to day time operation, for the fiber that is fed to the hydrolyzer.

It has also been determined that the fiber requires time for the moisture that is added to become equilibrated throughout the entire fiber particle, It has been determined that under laboratory conditions, it may take from 5 to 9 minutes to equilibrate the moisture content of the fiber. Under the industrial conditions it will be longer. Preferably, the autohydrolysis reaction time in the vessel is typically about 5 to 6 minutes or less. Accordingly it is preferred that a soaking or impregnation stage is conducted prior to the autohydrolysis reaction.

Accordingly, embodiments of the present invention relate to a cellulosic feedstock pre-treatment process, which comprises the addition of moisture to a cellulosic feedstock to prepare the feedstock for pre treatment (i.e. autohydrolysis). More specifically, embodiments of the present invention involve determining an amount of moisture to be added to a cellulosic feedstock to obtain a predetermined moisture content in the cellulosic feedstock that may then be subjected to an autohydrolysis reaction and a subsequent steam explosion.

In one broad aspect, a method is provided for treating a cellulosic feedstock, such as for subsequent ethanol production. The method comprises determining an initial moisture content of the cellulosic feedstock; adding an amount of moisture to the cellulosic feedstock to obtain a predetermined moisture content of the cellulosic feedstock; and subsequently subjecting the cellulosic feedstock to hydrolysis, preferably autohydrolysis followed by enzymatic hydrolysis.

Embodiments in accordance with this broad aspect may be advantageous because the moisture content of the cellulosic feedstock may be monitored and controlled to prevent the feedstock having an excess of moisture, which may result in an incomplete autohydrolysis and/or accumulation of degraded sugars in the reactor or an insufficient amount of water that will hinder activation and may result in a portion of the cellulosic feedstock not having the water molecule present for the autohydrolysis reaction to occur.

In some embodiments, the step of adding an amount of moisture to the cellulosic feedstock comprises determining the amount of moisture required to obtain the predetermined moisture content based on the weight of the cellulosic feedstock and the initial moisture content of the cellulosic feedstock, and adding the amount of moisture.

In some embodiments, the steps of determining the initial moisture content and adding the amount of moisture are performed automatically and/or continuously.

In some embodiments, the initial moisture content is less than 15 wt % based on the total weight of the cellulosic feedstock. In further embodiments, the predetermined moisture content is about 30 to 60 wt % based on the total weight of the cellulosic feedstock.

In some embodiments, the method further comprises determining a weight of the cellulosic feedstock as the cellulosic feedstock is conveyed to a mixing vessel.

In some embodiments, the method further comprises conveying the cellulosic feedstock through a mixing vessel, and adding at least a portion of the amount of moisture to the cellulosic feedstock while the cellulosic feedstock is conveyed through the mixing vessel.

In some embodiments, the method further comprises adding moisture to the cellulosic feedstock through multiple inlet ports provided on the mixing vessel.

In some embodiments, the method further comprises completing addition of the amount of moisture prior to conveying the cellulosic feedstock through a downstream portion of the mixing vessel.

In some embodiments, the method further comprises adding at least a portion of the amount of moisture prior to conveying the cellulosic feedstock through a mixing vessel.

In some embodiments, the method further comprises passing the cellulosic feedstock downwardly into the mixing vessel while exposing the cellulosic feedstock to droplets of water of between 600μ and 6000μ in diameter.

In some embodiments, the method further comprises heating the cellulosic feedstock while conveying the cellulosic feedstock through a mixing vessel, and completing addition of the amount of moisture prior to conveying the cellulosic feedstock through a downstream portion of the mixing vessel, wherein the cellulosic feedstock has a temperature less then 50° C. prior to entering the mixing vessel and a temperature from 50° C. to 70° C. after exiting the mixing vessel.

In some embodiments, the method further comprises adding a hydrolysis catalyst with the moisture.

In some embodiments, the cellulosic feedstock is heated while the amount of moisture is added.

In some embodiments, the initial moisture content of each segment of cellulosic feedstock is determined and the amount of moisture to obtain a predetermined moisture content is provided to that segment of the cellulosic feedstock.

In another broad aspect, a cellulosic feedstock treatment apparatus is provided. The apparatus comprises a moisture sensor that provides an output value corresponding to an initial moisture content of the cellulosic feedstock. The apparatus further comprises a weight scale that provides an output value corresponding to a weight of the cellulosic feedstock. A processor is coupled to the moisture sensor and the weight sensor. The processor is configured to determine an amount of moisture to be added to the cellulosic feedstock based on the weight of the cellulosic feedstock and the initial moisture content of the cellulosic feedstock to obtain treated cellulosic feedstock having a predetermined moisture content. A mixing vessel is provided downstream from the weight sensor.

In some embodiments, the weight sensor comprises a weighing conveyor.

In some embodiments, the mixing vessel comprises a longitudinally extending volume having an inlet, an opposed outlet, and a conveyance member positioned inside the volume.

In some embodiments, the apparatus comprises a passage extending from the weight sensor to the inlet wherein at least a portion of the passage extends downwardly. In further embodiments, the portion comprises at least one moisture injection port. In some embodiments, at least one moisture injection port is configured to provide discrete droplets of water of between 600µ and 6000µ in diameter.

In some embodiments, an upstream portion of the mixing vessel has multiple water injection ports. In further embodiments, a downstream portion of the mixing vessel has an absence of water injection ports.

In some embodiments, the mixing vessel has a heating jacket.

In some embodiments, the apparatus comprises a downstream autohydrolysis reactor.

In some embodiments, the processor provides a signal to at least one moisture addition member and the signal is lagged by an amount of time corresponding to the time for a segment of cellulosic feedstock to travel from the moisture sensor to a moisture addition zone containing the at least one moisture addition member.

In some embodiments the conveyance member comprises paddles (or flights) mounted on a shaft wherein steam may flow through the paddles and or shaft. Accordingly, the feedstock may be indirectly heated by the paddles and/or shaft. Alternately, moisture injection ports may be provided in the shaft and/or paddles.

BRIEF DESCRIPTION OF THE DRAWINGS

These and other advantages of the present invention will be more fully and particularly understood in connection with the following description of the preferred embodiments of the invention in which.

DETAILED DESCRIPTION OF THE INVENTION

Figure 1:
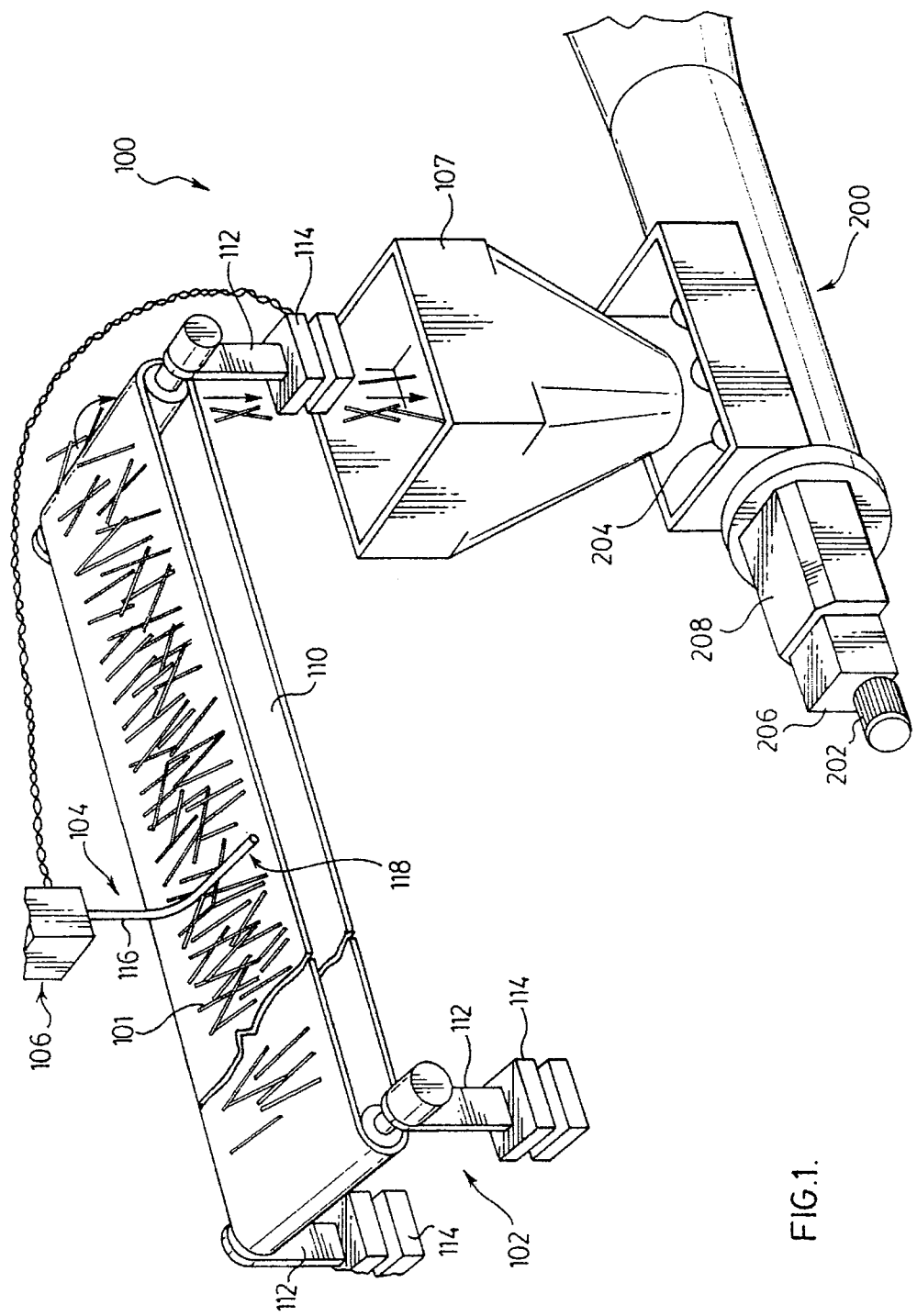
FIG. 1 is a partial perspective illustration of an embodiment of an apparatus of the present invention.
Figure 2:
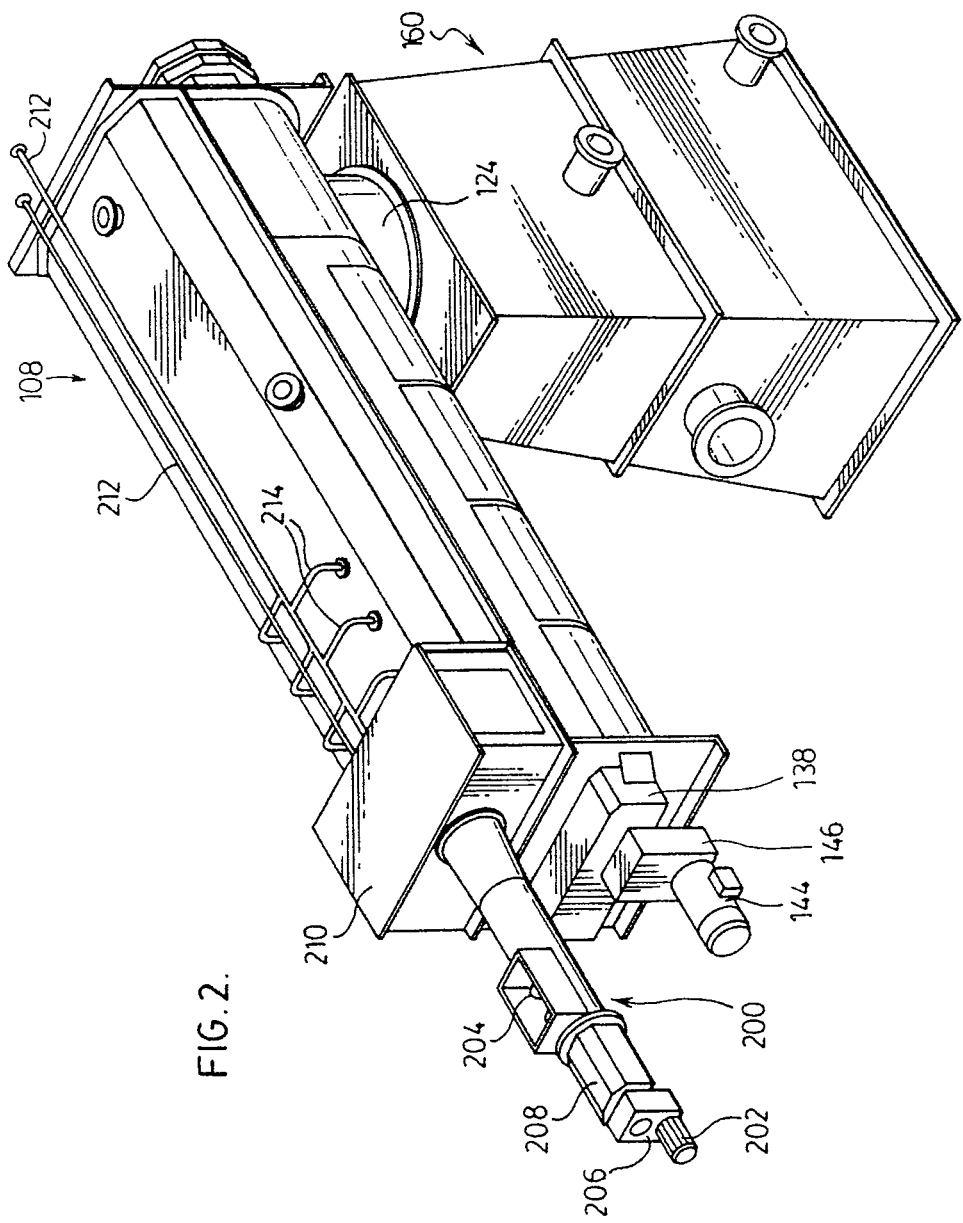
FIG. 2 is a perspective illustration of an embodiment of a mixing vessel of an apparatus of the present invention.
Figure 3:
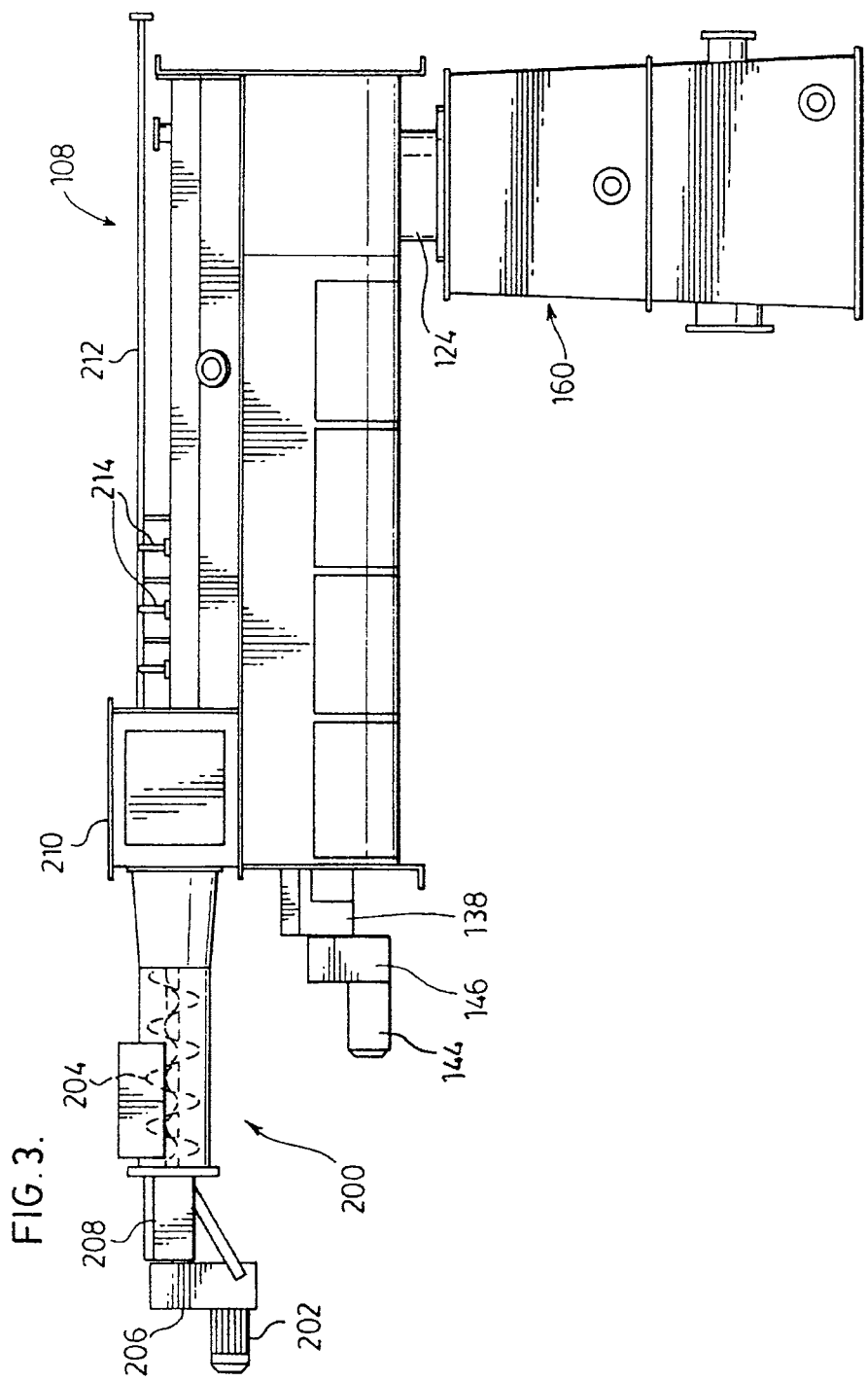
FIG. 3 is a side plan view of the mixing vessel of FIG. 2.
Figure 4:
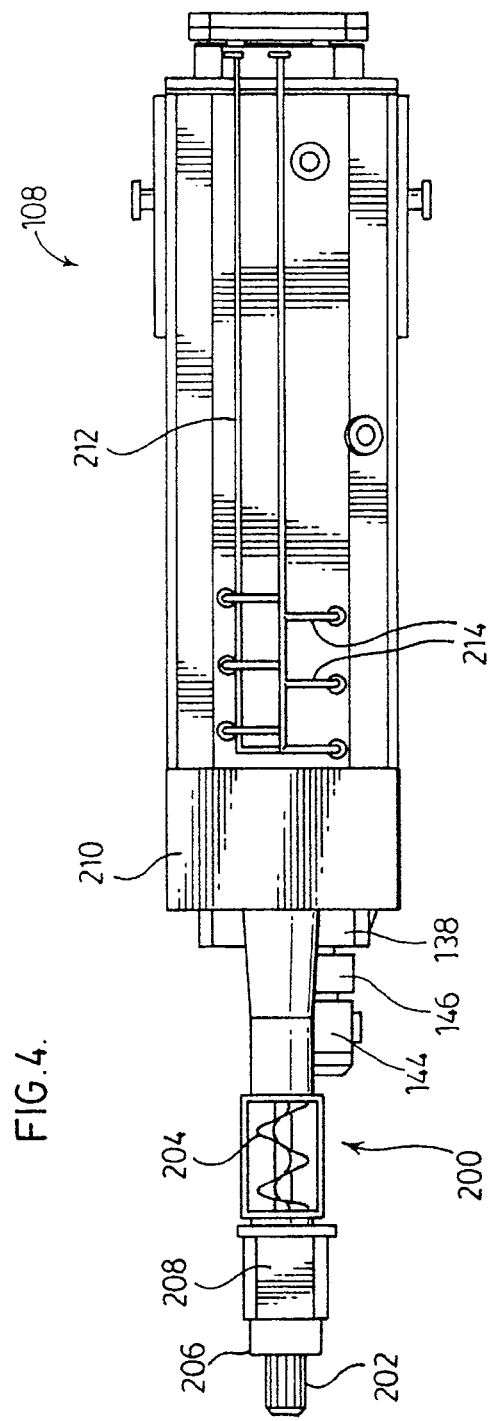
FIG. 4 is a top plan view of the mixing vessel of FIG. 2.

Referring to FIGS. 1 to 8, an embodiment of an apparatus 100 of the present invention is shown. Apparatus 100 comprises a weight sensor 102, a moisture sensor 104, a processor 106, and mixing vessel 108. Apparatus 100 is usable to determine if an amount of moisture needs to be added to a cellulosic feedstock to obtain a predetermined moisture content in the cellulosic feedstock, and preferably to add the amount of moisture to the cellulosic feedstock if such is required.

The cellulosic feedstock is preferably a lignocellulosic feedstock. A lignocellulosic feedstock is derived from plant materials. As used herein, a "lignocellulosic feedstock" refers to plant fiber containing cellulose, hemicellulose and lignin. In some embodiments, the feedstock may be derived from trees, preferably deciduous trees such as poplar (e.g., wood chips). Alternately or in addition, the feedstock may also be derived from agricultural residues such as, but not limited to, corn stover, wheat straw, barley straw, rice straw, switchgrass, sorghum, bagasse, rice hulls and/or corn cobs. Preferably, the lignocellulosic feedstock comprises agricultural residues and wood biomass, more preferably wood biomass and most preferably deciduous. The applicants contemplate other sources of plant materials comprising cellulose, hemicellulose and/or lignin, such as algae, for use in deriving cellulosic feedstocks and any of those may be used.

The lignocellulosic feedstock is preferably cleaned, e.g., to remove ash, silica, metal strapping (e.g., from agricultural products), stones and dirt. The size of the components of the lignocellulosic feedstock may also be reduced. The size of the components of the feedstock may be from about 0.05 to about 2 inches, preferably from about 0.1 to about 1 inch, and more preferably from about 0.125 to about 0.5 inches in length. Any process machinery that is able to crush, grind or otherwise decrease the particle size may be utilized.

In order to produce a feedstock having a predetermined moisture content, the starting moisture content of the feedstock must be known and the amount of water addition that is required must be determined. In accordance with one aspect of this invention, the starting moisture content is determined by utilizing a moisture sensor to determine the starting moisture content. The amount of water addition that is required may be determined using the starting moisture content and the amount of feedstock having that moisture content that is provided to the process. The measurements may be made on a continuous basis or by sporadic sampling.

As exemplified in FIG. 1, weight sensor 102 is configured to weigh the cellulosic feedstock 101 that is provided to apparatus 100, and to provide an output value corresponding to a weight of the cellulosic feedstock 101 on the weight sensor 102. In some embodiments, weight sensor 102 is further configured to continuously convey and weigh the cellulosic feedstock 101. For example, in the embodiment shown, weight sensor 102 is a weighing conveyor, which comprises a conveyor belt 110, which rests on supports 112. Supports 112 each comprise a scale 114, for weighing the cellulosic material 101 resting on the conveyor belt at a given moment in time. In this embodiment, cellulosic feedstock 101 is continuously deposited on the conveyor belt, and is conveyed towards mixing vessel 108 as scales 114 continuously weigh the cellulosic feedstock 101.

In embodiments wherein weight sensor 102 is operated in a continuous fashion, the output value provided by weight sensor 102 may correspond to the weight measured at a given moment in time. For example, in some embodiments, weight sensor 102 may measure the weight of the cellulosic feedstock 101 on conveyor belt 110 every 0.5 seconds. By computation processor 106 determines the exact weight of water to be added to reach the desired moisture set point. The output value is sent to processor 106, as will be further described hereinbelow, and may additionally or alternately be displayed, for example on a screen (not shown).

In operation of this preferred embodiment, the measurement of the moisture is taken on a continuous basis as the fiber is conveyed by the weighing conveyor. Simultaneously the weighing conveyor measures the total weight of the fiber on the weighing conveyor, namely the weight of the fiber as well as the water in the fiber structure. This information, as well as information as to the amount of fiber leaving and/or being added to conveyor belt 110 per unit time is provided to processor 106. For example, processor 106 may be programmed with the speed of conveyor belt 110. Accordingly processor 106 can determine the weight of fiber entering hopper 107 per unit time as well as the moisture content of that fiber. Preferably, processor 106 is also provided with information as to the amount of time required for the fiber leaving conveyor belt 110 to enter a zone (e.g., mixing vessel 108) at which moisture is added to the fiber. Processor 106 may accordingly provide a signal adjusting the amount of moisture added to the fiber passing through the moisture addition zone.

Preferably, processor 106 may provide a time delay signal adjusting the amount of moisture added to a particular segment of fiber passing through the moisture addition zone. These signals may be continuously processed such that the amount of moisture added to each segment of fiber is premised upon the actual moisture content of that segment of fiber fiberfiber Accordingly the required moisture addition in the subsequent impregnation step may be controlled to obtain the desired final total moisture content prior to autohydroysis.

In alternate embodiments, weight sensor 102 may be another type of weight sensor, for example a stationary balance, which the cellulosic feedstock is deposited onto and removed from in a batch-type process. For example, a hopper or other storage vessel may be provided with a known weight of feedstock, which is then provided to conveyor belt 110. Alternately, the hopper or storage vessel may be weighed and the feedstock may then be provided to conveyor belt 110. It will be appreciated that the feedstock may be weighed after the moisture content is determined (e.g., hopper 107 may be weighed). In embodiments wherein weight sensor 102 is operated in a batch-type fashion, the output value may correspond to the weight of a given batch.

As exemplified in FIG. 1, moisture sensor 104 is configured to measure the moisture content of the cellulosic feedstock provided to apparatus 100 (referred to hereinafter as the initial or starting moisture content). The initial moisture content will depend on numerous factors, such as the nature of the cellulosic feedstock and any storage conditions and upstream processes to which it has been subjected. However, in some embodiments, the initial moisture content is less than about 15 wt %.

In the embodiment shown, moisture sensor 104 is an electronic moisture sensor, such as Doscher & Doscher moisture scan or Acrowood moisture analyzer, which is provided in the distal region 118 of a probe 116. Distal region 118 is positioned adjacent conveyor belt 110, and measures the moisture content of the cellulosic feedstock as it is preferably weighed by weight sensor 102. In alternate embodiments, moisture sensor may be otherwise configured. For example, moisture sensor 104 may be a microwave moisture sensor, and therefore may not directly contact the cellulosic feedstock 101 or conveyor belt 110.

Processor 106 is coupled to moisture sensor 104 and weight sensor 102. Although cables are shown to connect moisture sensor 104 and weight sensor 102 to processor 106, it is contemplated that wireless connections may be provided. Processor 106 is configured to determine an amount of moisture to be added to the cellulosic feedstock based on the weight of the cellulosic feedstock, and the initial moisture content of the cellulosic feedstock to obtain a cellulosic feedstock having a predetermined moisture content. That is, processor is coupled to receive the output of the weight sensor 102 and the moisture sensor 104, and based on these outputs, determine the amount of moisture to be added to the cellulosic feedstock in a downstream pre-treatment process. For example, in some embodiments, the predetermined moisture content of the cellulosic feedstock may be between about 30 wt % and 60 wt %. If the weight of the cellulosic feedstock is about 10 kg, and the moisture content is about 10%, then the amount of moisture to be added to the cellulosic feedstock may be between about 3 kg and 12 kg.

The amount of moisture added is preferably determined and more preferably controlled by processor 106, in order to obtain cellulosic feedstock of a predetermined moisture content. That is, processor 106 may determine the amount of moisture to be added to the cellulosic feedstock, and may display this amount, such that it may be added manually, or the processor may be connected to the mixing vessel, such that the amount may be added automatically. In an optional embodiment, the values obtained from moisture sensor 104 and weight sensor 102 may be provided to an operator who may then determine the amount of water to be added, based on a table, chart, or by using a calculation.

The moisture is preferably added as liquid water, but may be added as steam. Preferably, water is provided as discrete droplets of water, preferably between $600\mu$ and $6000\mu$ in diameter, and preferably from multiple locations.

In some embodiments, additional components, such as one or more hydrolysis catalysts, such as organic and/or inorganic acids, caustic soda, and the like, may be added together with the moisture.

Referring to FIGS. 2 to 8, mixing vessel 108 is preferably provided downstream from weight sensor 102. Moisture may be added to the cellulosic feedstock in mixing vessel 108 and/or upstream from mixing vessel 108 (i.e. between weight sensor 102 and mixing vessel 108) as will be described further herein.

Preferably, at least some of the moisture is added in mixing vessel 108. Accordingly, mixing vessel 108 may be above atmospheric pressure. Moisture (as water or steam) may accordingly flow upstream to exit mixing vessel 108 unless the inlet to mixing vessel 108 inhibits such flow. In the embodiment shown, impregnator feeder 200 is preferably positioned upstream of mixing or impregnation vessel 108 and may be any feeder that inhibits, and preferably prevents, the flow of moisture upstream. A rotating valve or the like may be provided to segment such upstream flow. Preferably impregnation feeder is a screw feeder comprising a motor 202 drivingly connected to a screw or auger 204, such as via a transmission or gear reduction assembly provided in housing 206. The shaft on which screw 202 is provided may be rotatably mounted in housing 208 such that augur 204 is a cantilevered plug screw conveyor. Accordingly, feeder 200 produces a plug of material that prevents upstream migration of moisture. The plug may be conveyed into inlet housing 210 that is mounted, e.g., to the upper surface of mixing vessel 108. The feedstock may then pass downwardly into mixing vessel 108. In other embodiments, impregnator feeder 200 may not be used.

In the embodiment shown, mixing vessel 108 comprises a longitudinally extending volume 120 having an inlet at one end (e.g., positioned within or below inlet housing 210), and an opposed outlet, which may be an opening in the bottom of mixing vessel above outlet passage 124. A conveyance member 126 is preferably positioned inside volume 120. In the embodiment shown, conveyance member 126 preferably comprises two rotary shafts 128, having a plurality of paddles 130 extending outwardly therefrom. In use, rotary shafts 128 of conveyance member 126 are rotated, such that paddles 130 engage the cellulosic material within volume 120 and urge the cellulosic material from the inlet towards outlet 124 while mixing the cellulosic material. In other embodiments, conveyance member 126 may be otherwise configured. For example, conveyance member 126 may comprise one or more longitudinally extending augers, single screw conveyor with paddles, ribbon screw conveyor, standard screw conveyor with tabbed flights and bars, and the like. In addition, vessel 108 need not extend horizontally but may be angled downwardly so that gravity assists the travel of the feedstock through vessel 108. As exemplified in FIG. 2, conveyance members 126 may be drivenly connected to a motor 144. As exemplified, motor 144 is drivingly connected to conveyance members 126 via a transmission or gear reduction assembly provided in housing 146. The gear reduction assembly may be drivingly connected to ends 137 of conveyance members 126 that are positioned inside housing 138.

A hopper 107 is preferably provided between weight sensor 102 and feeder 200, in order to funnel the cellulosic material from weight sensor 102 into mixing vessel 108. Any other passage or feeder known in the art may be used. Accordingly, hopper may feed cantilevered plug screw conveyor 200 immediately prior to impregnator vessel 108.

In some embodiments, some or all of the moisture may be added to the cellulosic feedstock while the cellulosic feedstock is conveyed through feeder 200. For example, some of the moisture may be added to lubricate the flow of the feedstock through feeder 200.

Alternately, or in addition, some or all of the moisture may be added to the cellulosic feedstock while the cellulosic feedstock is conveyed through mixing vessel 108. In such embodiments, mixing vessel 108 may comprise multiple moisture injection ports 132. For example, as exemplified in FIG. 2, a plurality of injection ports may be provided in the upper portion of mixing vessel 108. As shown therein, one or more conduits 212 may convey water to a plurality of branch conduits 214 extending to different locations on the upper portion of mixing vessel 108. The end of these conduits are in fluid flow communication with the interior of mixing vessel 108, via a moisture addition member such as a nozzle or an open ended pipe or the like. As exemplified, six ports are provided. However, additional or fewer ports may be used. Accordingly, moisture injection ports may be provided in the inner surface 150 of shell 152 of vessel 108.

Alternately, or in addition, referring to FIGS. 7A-7D, in the embodiment shown, paddles 130 of conveyance member 126 comprise one or more injection ports 132. A fluid conduit, which may be interior volume 134 of each rotary shaft 128, provides fluid communication between moisture injection ports 132 and a fluid source (not shown), which may be coupled to ends 137 of rotary shafts 128 that are mounted in housing 138. The fluid conduit may be external to shaft 128 or a separate passage inside shaft 128. Alternately, or in addition, moisture injection ports 132 may be provided in the outer surface of rotary shafts 128 (see FIG. 5).

Preferably, shaft 128 and paddles 130 are not provided with injection ports 132. However, a heated fluid is preferably conveyed through shaft 128 and/or paddles 130 so as to provide indirect heat to the feedstock in mixing vessel 108.

As exemplified, paddles 130 are secured to shafts 128 by rods 154. Paddles 130 may be secured to one end of rods 154 by any means known in the art, such as welding, or mechanical affixation members such as rivets, or screws. The other end of rod 154 may be provided by a screw thread on which bolt 156 may be received. Rods 154 may be secured to shaft 128 such as by extending transversely through shaft 128 from one side to the other and bolt 156 secured thereon. Suitable packing, gaskets or the like may be provided to limit or prevent moisture leaking out of shaft 128 past rod 154. Rod 154 may be provided with one or more openings 158 in fluid communication with volume 134 inside shaft 128. Accordingly, moisture may flow through shaft 128, through rod 154 to paddle 130 and out through ports 132 into volume 120 of vessel 108. However, paddles 130 may be directly secured to shafts 128 or may be secured by any other means known in the art.

In some embodiments, injection ports 132 are provided along the entire length L of mixing vessel 108. In other embodiments, moisture injection ports 132 are provided only in an upstream portion of mixing vessel 108, preferably in the upstream half of the length L of mixing vessel 108 and, more preferably in the first or upstream third $L_{1/3}$ of the length L of mixing vessel 108 (see FIG. 5).

In some embodiments moisture may additionally or alternately be added to the cellulosic feedstock upstream from mixing vessel 108. For example, referring to FIG. 1, a passage, which may comprise or consist of hopper 107, may be provided between conveyor belt 110 of weight sensor 102 and the inlet of the mixing vessel 108. In the embodiment shown, all of the passage extends downwardly. However, in alternate embodiments, only a portion of the passage may extend downwardly. The passage may comprise at least one, and preferably multiple, moisture injection ports. The moisture injection ports may be configured to inject a mist of moisture into the passage. For example, the interior wall of hopper 107 may be provided with moisture injection ports. Alternately, or in addition, a water outlet, such as one or more spray atomizers, may be provided inside hopper 107, preferably at an upper section thereof.

Figure 5:
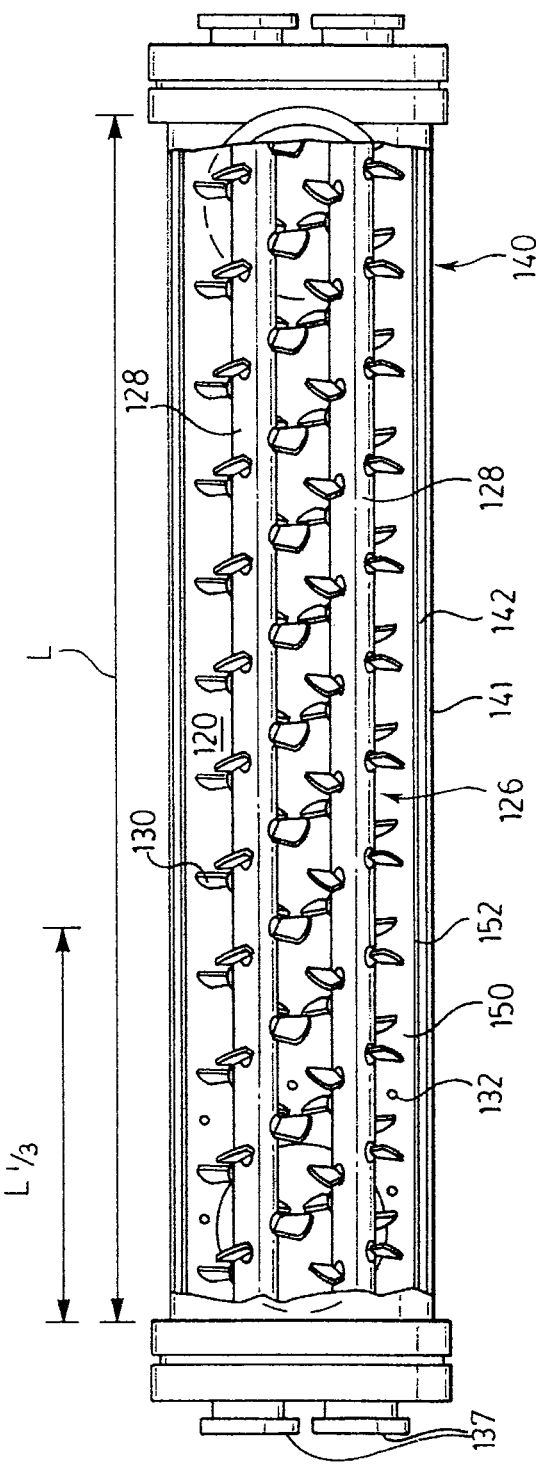
FIG. 5 is a cutaway top plan view of the mixing vessel of FIG. 2, wherein the upper portion of the shell has been removed showing a preferred embodiment of a conveyance member.
Figure 6:
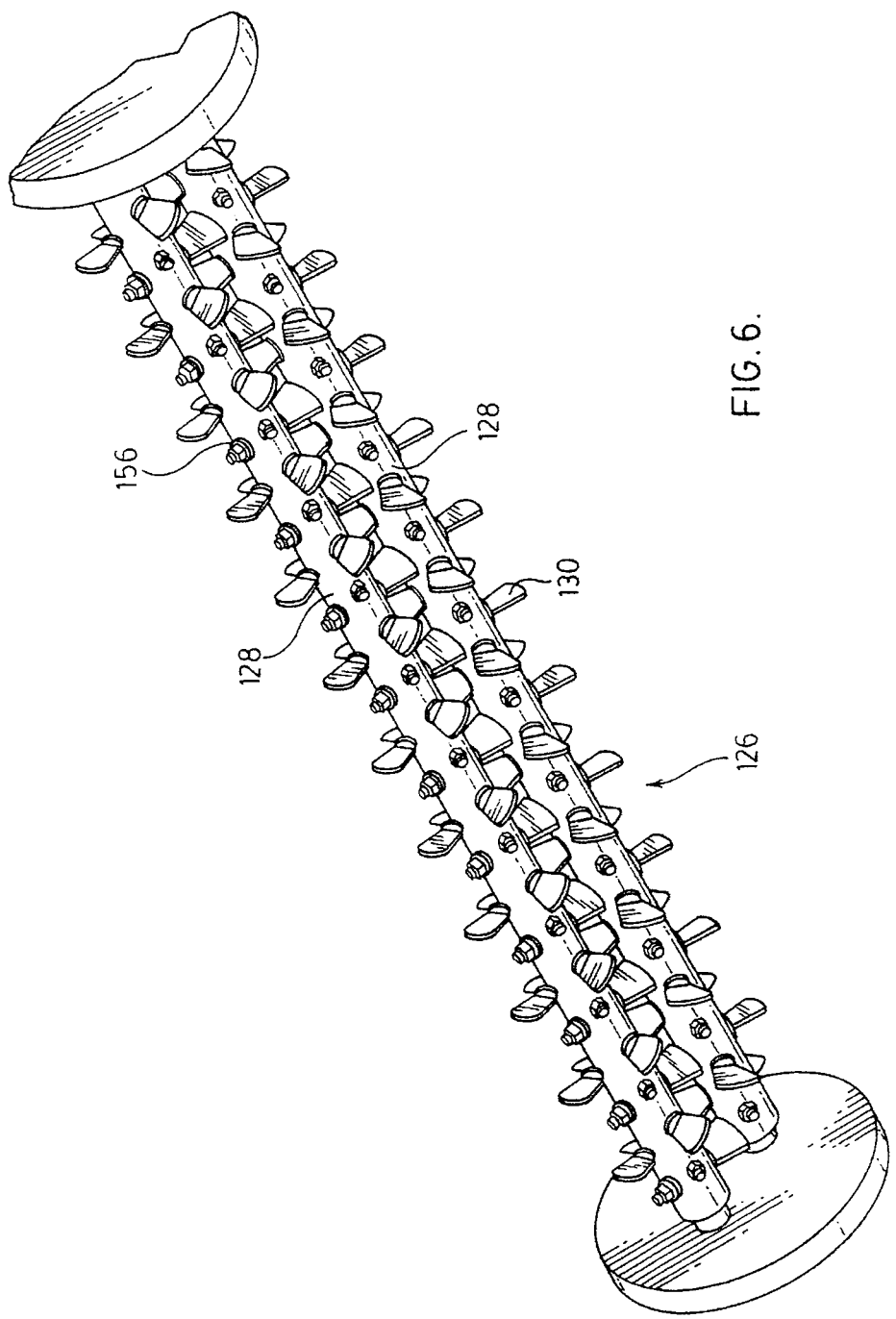
FIG. 6 is a perspective illustration of the conveyance member shown in FIG. 5.
Figure 7:
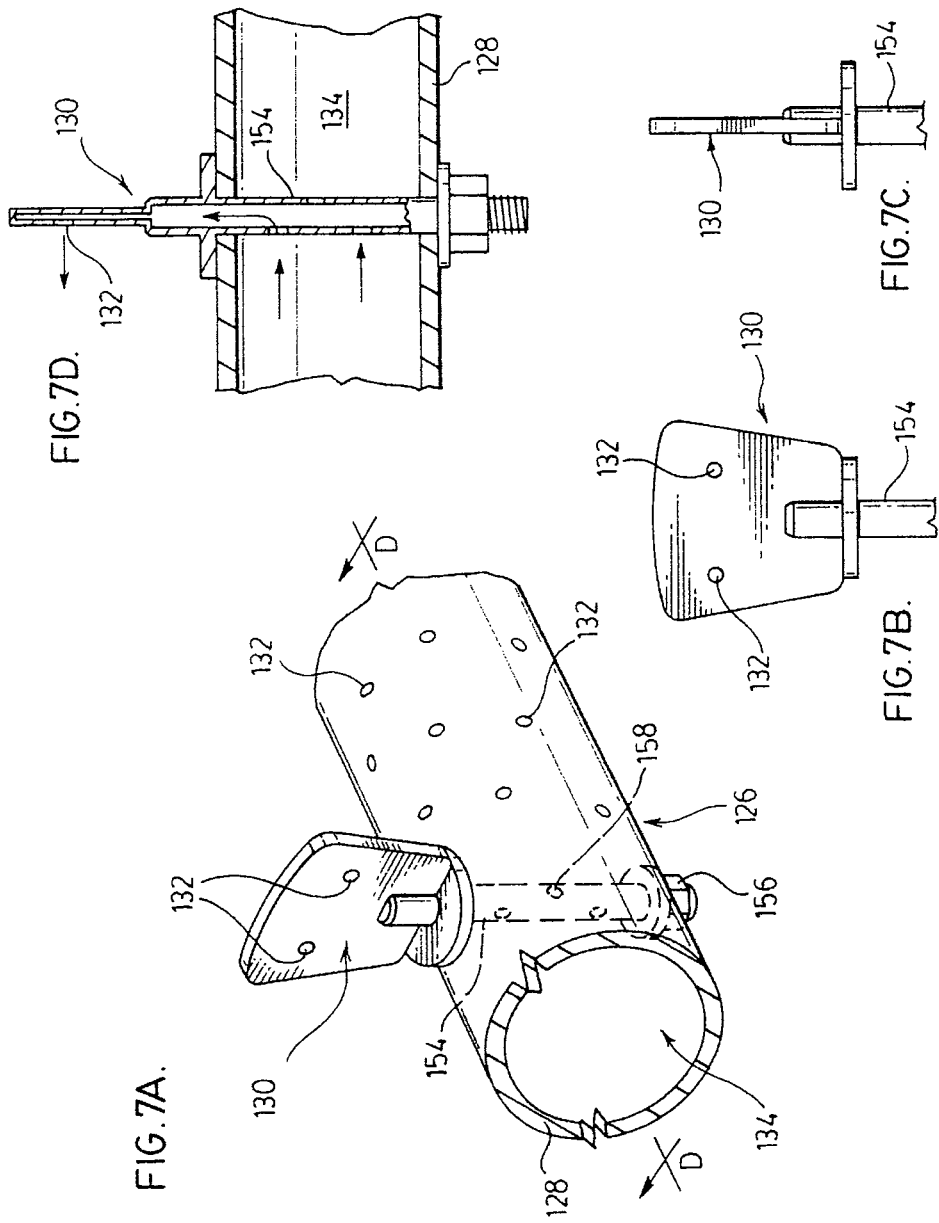
FIG. 7A is a partial perspective illustration of the conveyance member shown in FIG. 5, wherein the conveyance member optionally includes paddles having moisture injection ports.
FIG. 7B is a partial front plan view of the paddle shown in FIG. 7A.
FIG. 7C is a side plan view of the paddle shown in FIG. 7A.
FIG. 7D is a longitudinal cross-section taken along line D-D in FIG. 7A.

In some embodiments, as exemplified in FIG. 5, mixing vessel 108 may be provided with a heating jacket 140. Heating jacket 140 may be of any construction known in the art. For example, as exemplified, heating jacket 140 comprises an outer shell 141 defining an inner volume 142 extending between outer shell 141 and inner shell 152, through which a heated fluid, for example steam or heated water, is passed from a fluid source (not shown) in fluid communication with heated fluid inlet, through volume 142 to a cooled fluid outlet. In some embodiments, heating jacket 140 is configured to heat the cellulosic feedstock from less than about 50° C. (e.g. about 20° C.) at the inlet to between about 50° C. and about 70° C. at outlet 124.

Figure 8:
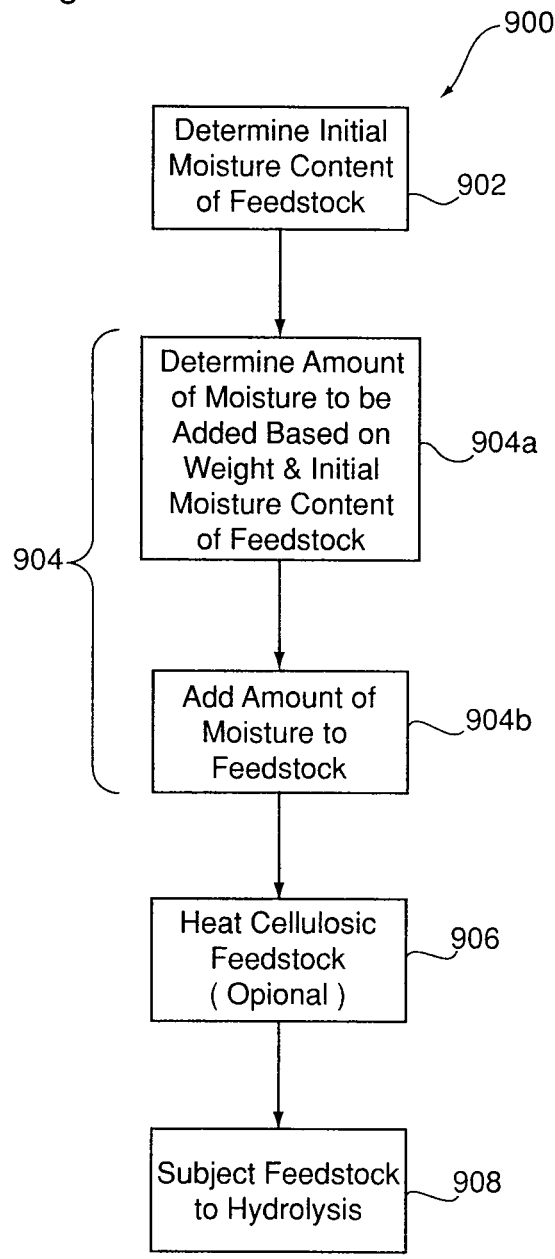
FIG. 8 is a flow chart showing steps of an embodiment of a method of the present invention.

Referring to FIG. 8, an embodiment of a method 900 for treating a cellulosic feedstock, such as for subsequent ethanol production, will presently be described. It will be appreciated that although method 900 is described with reference to apparatus 100, method 900 may be carried out with an alternate apparatus, and apparatus 100 may be used according to an alternate method. Furthermore, although method 900 is described as a continuous process, it will be appreciated that method may be carried out as a semi-continuous or batch process.

As previously mentioned, the cellulosic feedstock provided to method 900 may be varied and the initial moisture content of the cellulosic feedstock may vary depending on numerous factors. An initial moisture content of the cellulosic feedstock is determined (step 902). For example, as described previously, the cellulosic feedstock may be continuously conveyed past a moisture sensor 104. In some embodiments, wherein the cellulosic feedstock comprises straw, the initial moisture content may be less than about 15 wt % based on the total weight of the cellulosic feedstock. However, in alternate embodiments, the initial moisture content may be greater than 15 wt %.

Subsequently, an amount of moisture is added to the cellulosic feedstock to obtain a predetermined moisture content of the cellulosic feedstock (step 904). Step 904 preferably includes steps 904a and 904b. Step 904a comprises determining the amount of moisture to be added based on the weight of the cellulosic feedstock and the initial moisture content of the cellulosic feedstock. For example, once the weight of the material introduced to the process is known, and the moisture content of that material is know, the amount of water to be added may be determined by calculating the amount of water that is required to raise the moisture content of the material from the starting moisture content to the predetermined moisture content. This step may be conducted automatically by a computer, by a human operator using a calculator or a table, or any other means.

Step 904b comprises adding the required amount of moisture to the cellulosic feedstock. The moisture is preferably added at multiple locations so that the water is evenly distributed through the mass of the feedstock. Alternately, or in addition, the feedstock is preferably also mixed to assist in distributing the added moisture throughout the feedstock. For example, a mixing vessel, such as vessel 108, may be used to combine water with the feedstock and/or to mix a feedstock that has already had water added thereto. In accordance with the latter option, step 904b may comprise adding moisture to the cellulosic feedstock prior to conveying the cellulosic feedstock through a mixing vessel 108. For example, moisture may be added to the cellulosic feedstock as it is conveyed from a weighing and starting moisture determination station.

It is preferred that at least a portion of the mixing occurs without the addition of water. For example, the moisture is preferably added prior to conveying the cellulosic material through a downstream portion of mixing vessel 108, e.g., the half of vessel 108 immediately upstream of outlet 124. This permits more complete mixing of the added water and the feedstock and a greater uniformity of the moisture distribution of the feedstock at outlet 124.

Preferably, steps 902 and 904 are carried out automatically and continuously. That is, steps 902 and 904 are under preferably the control of a processor, such as processor 106, and are carried out as a continuous process, for example by conveying the cellulosic material past moisture sensor 104 on weighing conveyor 102.

Method 900 may optionally further comprise heating the cellulosic feedstock. For example, the cellulosic feedstock may be heated while the moisture is added, by providing mixing vessel 108 with a heating jacket 140 and/or providing a heating jacket to hopper 107 and/or by heating the required water that is added to the feedstock (step 906).

The cellulosic feedstock is preferably then subjected to activation (step 908). The hydrolysis reaction is preferably conducted by autohydrolysis, which, more preferably, is followed by enzymatic hydrolysis. Autohydrolysis may be carried out directly following steps 902-906, or after any number of intermediate steps. For example, from outlet 124 of mixing vessel 108, the cellulosic feedstock may be directed to a holding tank 160 where it is stored for a period of time at an elevated temperature to further enhance the uniformity of the moisture and heat distribution, prior to being passed to an autohydrolysis reactor.

It will be appreciated that certain features of the invention, which are, for clarity, described in the context of separate embodiments or separate aspects, may also be provided in combination in a single embodiment. Conversely, various features of the invention, which are, for brevity, described in the context of a single embodiment or aspect, may also be provided separately or in any suitable sub-combination.

Although the invention has been described in conjunction with specific embodiments thereof, if is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present invention.

We claim:

1. A cellulosic feedstock treatment apparatus, comprising:
   a) a moisture sensor providing an output value corresponding to an initial moisture content of a portion of the cellulosic feedstock;
   b) a weight sensor providing an output value corresponding to a weight of the portion of the cellulosic feedstock;
   c) a processor coupled to the moisture sensor and the weight sensor, the processor being configured to determine an amount of moisture to be added to the portion of the cellulosic feedstock based on the weight of the portion of the cellulosic feedstock and the initial moisture content of the portion of the cellulosic feedstock to obtain a treated cellulosic feedstock having a moisture content of between about 30 wt. % and 60 wt. % based on the total weight of the cellulosic feedstock;
   d) at least one moisture addition zone in which the amount of moisture is automatically added to the portion of the cellulosic feedstock, under the control of the processor; and
   e) a mixing vessel downstream from the weight sensor configured to allow the moisture to generally equilibrate through the cellulosic feedstock, the mixing vessel having a heating jacket configured to heat the cellulosic feedstock from less than about 50° C. at the mixing vessel inlet to between about 50° C. and about 70° C. at the mixing vessel outlet.

2. The apparatus of claim 1, wherein the weight sensor comprises a weighing conveyor.

3. The apparatus of claim 1, wherein the mixing vessel comprises a longitudinally extending volume having an inlet, an opposed outlet and a conveyance member positioned inside the volume.

4. The apparatus of claim 3, further comprising a passage from the weight sensor to the inlet wherein at least a portion of the passage extends downwardly.

5. The apparatus of claim 4, wherein the portion of the passage comprises at least one moisture injection port.

6. The apparatus of claim 5, wherein the at least one moisture injection port is configured to provide discrete droplets of water of between 600 μm and 6000 μm in diameter.

7. The apparatus of claim 4, wherein an upstream portion of the mixing vessel has multiple water injection ports.

8. The apparatus of claim 3, wherein a downstream portion of the mixing vessel has an absence of water injection ports.

9. The apparatus of claim 1, further comprising a downstream hydrolysis reactor.

10. The apparatus of claim 1, wherein the processor provides a signal to at least one moisture addition member and the signal is lagged by an amount of time corresponding to the time for the portion of the cellulosic feedstock to travel from the moisture sensor to the moisture addition zone containing the at least one moisture addition member.

11. The apparatus of claim 1, wherein the initial moisture content is less than 15 wt % based on the total weight of the cellulosic feedstock and the processor is configured to determine an amount of moisture to be added to the portion of the cellulosic feedstock based on the weight of the portion of the cellulosic feedstock and the initial moisture content of the portion of the cellulosic feedstock to obtain treated cellulosic feedstock having a moisture content between about 45 wt. % to 55 wt. % based on the total weight of the cellulosic feedstock.

12. The apparatus of claim 1, wherein at least a portion of the moisture is added upstream of the mixing vessel.

13. The apparatus of claim 1, wherein the moisture is added upstream of the mixing vessel.

14. The apparatus of claim 1, wherein the weight sensor continuously weighs the cellulosic feedstock and wherein the moisture sensor continuously measures the moisture content of the cellulosic feedstock.

* * * * *